United States Patent
Chi

(10) Patent No.: US 11,284,942 B2
(45) Date of Patent: Mar. 29, 2022

(54) SYSTEMS AND METHODS FOR CUSTOMIZED SPINE GUIDE USING TWO-DIMENSIONAL IMAGING

(71) Applicant: Charlie Wen-Ren Chi, Milpitas, CA (US)

(72) Inventor: Charlie Wen-Ren Chi, Milpitas, CA (US)

(*) Notice: Subject to any disclaimer, the term of this patent is extended or adjusted under 35 U.S.C. 154(b) by 168 days.

(21) Appl. No.: 16/687,530

(22) Filed: Nov. 18, 2019

(65) Prior Publication Data
US 2020/0155236 A1    May 21, 2020

Related U.S. Application Data

(60) Provisional application No. 62/917,114, filed on Nov. 19, 2018.

(51) Int. Cl.
| | |
|---|---|
| *A61B 17/70* | (2006.01) |
| *A61B 34/10* | (2016.01) |
| *A61B 17/00* | (2006.01) |
| *A61B 17/90* | (2006.01) |

(52) U.S. Cl.
CPC .......... *A61B 34/10* (2016.02); *A61B 17/7074* (2013.01); *A61B 17/90* (2021.08); *A61B 2017/00477* (2013.01); *A61B 2017/00526* (2013.01); *A61B 2034/102* (2016.02); *A61B 2034/107* (2016.02)

(58) Field of Classification Search
CPC combination set(s) only.
See application file for complete search history.

(56) References Cited

U.S. PATENT DOCUMENTS

| | | |
|---|---|---|
| 9,782,226 B2 | 10/2017 | Park et al. |
| 2017/0135706 A1* | 5/2017 | Frey .................. A61B 17/1671 |
| 2017/0354425 A1 | 12/2017 | Zaima et al. |

FOREIGN PATENT DOCUMENTS

CA        2917654 C        9/2018

OTHER PUBLICATIONS

International Searching Authority, International Search Report and Written Opinion, issued for International Application No. PCT/US2019/062260, dated Mar. 9, 2020 (11 pages).

* cited by examiner

*Primary Examiner* — Sameh R Boles
(74) *Attorney, Agent, or Firm* — Polsinelli PC; Derek D. Donahoe

(57) ABSTRACT

Aspects of present disclosures involve systems, methods, computer program products for creating a customized MIS spine guide using two-dimensional imaging. In particular, the present disclosure provides a method of creating customized implant or instrument trajectory guide using one or more two-dimensional (2D) images of the patient's vertebrae. The method for creating a customized MIS spine guide using two-dimensional imaging generally includes receiving a plurality of two-dimensional images of the patient's vertebrae from an imaging device, reformatting the two-dimensional images for surgical planning and creating a customized MIS spine guide from the 2D images, design a jig based at least on the placement of the mating shapes within the plurality of reformatted two-dimensional images by the computing device, and creating a customized spine guide using a milling machine or 3D printing device corresponding to the machine program.

16 Claims, 30 Drawing Sheets

SYSTEMS AND METHODS FOR CUSTOMIZED SPINE GUIDE USING TWO-DIMENSIONAL IMAGING

CROSS-REFERENCE TO RELATED APPLICATION

This application is related to and claims priority under 35 U.S.C. § 119(e) from U.S. Patent Application No. 62/917,114, filed Nov. 19, 2018 entitled "METHODS, SYSTEMS, COMPUTER PROGRAM PRODUCTS FOR CUSTOMIZED SPINE GUIDE USING TWO-DIMENSIONAL IMAGING," the entire contents of which is incorporated herein by reference for all purposes.

TECHNICAL FIELD

Aspects of the present disclosure generally relate to systems and methods for creating and manufacturing customized surgical guides. More specifically, the present disclosure relates to methods for creating spinal guides customized to a particular patient from one or more two-dimensional images of a patient's spine taken from an imaging device

BACKGROUND

Through repeated heavy lifting, traumatic events, bone disease and/or arthritis, a patient's spine may become degenerated, damaged or loosened to the point that pain or paralysis does not respond to medication or other forms of non-surgical treatments. One type of procedure to address the patient's back pain or deformity is spinal fusion. A spinal fusion procedure involves the implantation of pedicle screws through the left and right pedicles of the patient's vertebrae and metal plates or rods to stabilize both the ventral and dorsal aspects of the spine to improve stability and reduce pain. The pedicle represents the strongest point of the attachment of the spine, permitting significant forces to be applied without failure of the bone-screw interface.

Current methods of spinal fusion carry a significant risk of vascular, visceral and neurological injury caused by inaccurate placement of pedicle screws, implants or instruments. For example, given the different patient demographics and surgical techniques, such as minimally invasive surgery (MIS), studies have shown that pedicle screw misplacement can be as high as 40%. Misaligned pedicle screw problems range from minor issues to more serious problems, such as lack of spinal integrity and resulting in paralysis, fatalities, or other serious health issues.

A primary cause of misplacement is the surgeon's inability to accurately align the pedicle screw and provide it with an appropriate trajectory given the particular spinal geometry involved and MIS surgical technique. The goal is to achieve 5-wall bony continuity. For example, the pedicle screw is completely surrounded on all sides by bone; the bottom of the screw abuts and is located within a bony floor. From an anatomical perspective, providing a 5-wall bony continuity with proper trajectory will optimally place the fixation device within the pedicle, regardless of the design characteristics of the implant or instrument.

Typical placement of spinal implant involves passing the pedicle screw through the superior facet and also through the pedicle; the tip of the implant may then be fastened to the vertebral body. Typically, spinal surgeons using free-hand trajectory analysis or two-dimensional (2D) fluoroscopic images without guides or templates have performed this procedure.

Many of the current image-based patient matched, robotic-assisted, and computer navigation technologies for spinal procedures use what is characterized as "full segmentation" in order to represent a relevant portion of the vertebral spine surface in three-dimensions. This approach requires the use of dense, three-dimensional (3D) meshes to accurately represent the surface, especially a surface having cusps or sharp corners with very small associated radii or curvature. This approach has several disadvantages, including the following: (1) this approach is time consuming, often requiring hours of intense numerical work to generate and check the accuracy of the segmentation for a single surface; (2) because of time and computation processing required to implement this approach for a single surface, use of this approach in mass manufacturing of custom or semi-custom instruments and implants is limited; (3) this approach may introduce geometric errors, including closing errors; (4) because of the close spacing of grid points, polynomials of high math degree are used, which can introduce undesirable "ripples" in the mathematical surface produced by a full-segmentation process; and (5) formation and analysis of a large number of MRI or CT slices is required.

It is with these observations in mind, among others, that aspects of the present disclosure were conceived.

SUMMARY

The present inventions generally relate to systems, methods and computer program products for customized minimally invasive (MIS) spine instruments, guides, or jigs using two-dimensional imaging to treat patients suffering spinal disorders. Some of the common types of spinal procedure may include foraminotomy, laminectomy, spinal disc replacement, spine fusion, disctectomy, scoliosis, vertebral compression fracture.

One aspect of the present disclosure may provide a method for creating a MIS customized spine guide which includes receiving a plurality of two-dimensional (2D) images of the patient's vertebrae, reformatting the 2D images to approximate true anatomical or global coordinate system of the patient's vertebra, and locating a plurality of mating shapes within the reformatted plurality of 2D images corresponding to a plurality of mating shapes of a guide or jig for use during the spinal procedure. The method may also include the operations of generating a machining program based at least on the placement of the mating shapes within the plurality of reformatted 2D images and manufacturing the spine guide using a Computer Numerically Controlled (CNC) or 3D printing machines based at least on the generated machine program.

Another aspect of the present disclosure may take the form of a system for creating a customize MIS spine guide for a spinal procedure from a plurality of 2D images which includes a network connection receiving a plurality of 2D images of the patient's vertebrae, the plurality of 2D images generated utilizing an imaging device and a computing device. The computing device may comprise at least one processing device and a non-transitory memory device in communication with the at least one processing device for storing one or more instructions that, when executed by the least one processing device, cause the computing device to perform certain operations. Such operations may include reformatting at least a portion of the 2D images to approximate a true anatomical coordinate or global coordinate system of the patient's vertebra, locating a plurality of mating shapes within the reformatted plurality of 2D images, the plurality of mating shapes corresponding to a plurality of mating shapes of the spine guide for use during the spinal procedure, creating a jig or guide based at least on the placement of the mating shapes within the plurality of reformatted 2D images, generating a machine program based at least on the placement of the mating shapes within the reformatted plurality of 2D images, and transmitting the machining program over the network connection to a CNC or 3D printing machine for manufacturing the customized spine guide based at least on the generated machine program.

Yet another aspect of the present disclosure relates to code implemented in a non-transitory, computer readable medium that when executed by a processor, is operable to perform operations including receiving, at a computing device, a plurality of two-dimensional images of a patient's vertebrae that is the subject of a spinal procedure and reformatting the two-dimensional images, via an identification of a plurality of portions of the patient's vertebrae within the plurality of two-dimensional images, to approximate a true anatomical coordinate of the patient's vertebrae. The code is further operable to locate a plurality of mating shapes within the reformatted plurality of two-dimensional images of the patient's vertebrae, the plurality of mating shapes corresponding to a plurality of mating shapes of an implant jig for use in implanting a pedical screw into the patient's vertebrae during the spinal procedure and transmit, to a milling device, a milling program based at least on the placement of the mating shapes within the reformatted plurality of two-dimensional images of the patient's vertebrae.

There has thus been outlined, rather broadly, some of the features of the methods, systems, computer program products for a customized MIS spine guide using 2D imaging in order that the detailed description thereof may be better understood, and in order that the present contribution to the art may be better appreciated. There are additional features of the methods, systems and computer program products for creating a customized MIS spine guide using 2D imaging that will be described hereinafter and that will form the subject matter of the claims appended hereto. In this respect, before explaining at least one aspect of the methods, systems, computer program products for a customized MIS spine guide using 2D imaging in detail, it is to be understood that the methods, systems, computer program products for a customized MIS spine guide using 2D imaging is not limited in its application to the details of construction or to the arrangements of the components set forth in the following description or illustrated in the drawings. The methods, systems, computer program products for a customized MIS spine guide using 2D imaging is capable of other aspects and of being practiced and carried out in various ways. Also, it is to be understood that the phraseology and terminology employed herein are for the purpose of the description and should not be regarded as limiting.

BRIEF DESCRIPTION OF THE DRAWINGS

The various features and advantages of the technology of the present disclosure will be apparent from the following description of particular embodiments of those technologies, as illustrated in the accompanying drawings. It should be noted that the drawings are not necessarily to scale; however the emphasis instead is being placed on illustrating the principles of the technological concepts. The drawings depict only typical embodiments of the present disclosure and, therefore, are not to be considered limiting in scope.

DETAILED DESCRIPTION

Figure 1:
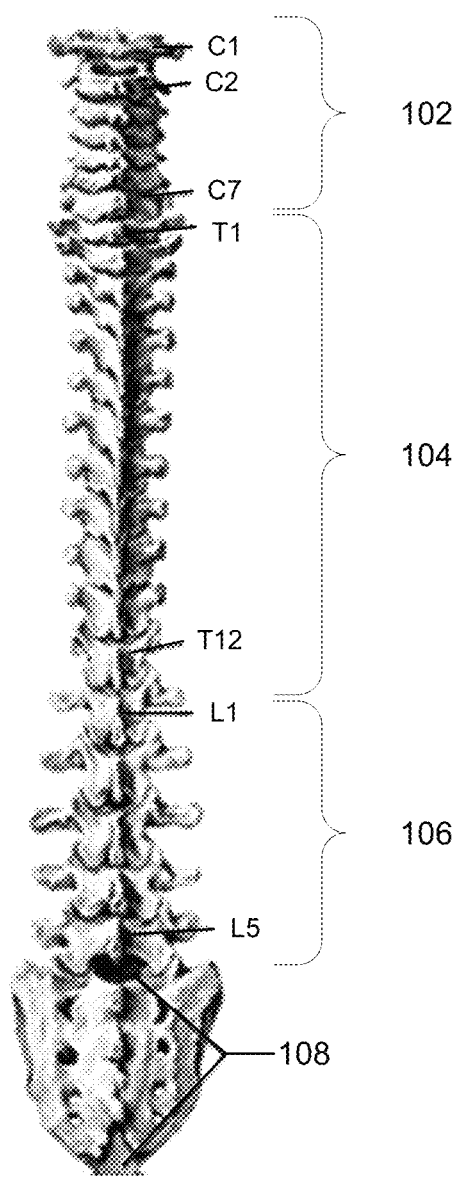
FIG. 1 is a posterior view of the human spine.

Aspects of the present disclosure involve systems, methods, computer program products, manufacture process and the like for customized minimally invasive surgical (MIS) spine guides, instruments or jigs. In particular, the present disclosure provides for a method of creating a customized MIS spine guide from one or more two-dimensional (2D) images of the patient's vertebrae to undergo the spinal procedure. The method includes receiving the 2D images of the vertebral segments from an imaging device, reformatting the images, and creating a customized MIS trajectory guide from the images. In general, one or more landmarks are electronically marked on one or more of the series of 2D images of the patient's vertebrae through a computing device. These electronic markers on the series of 2D images correspond to landmarks of the patient's vertebra to undergo the spinal procedure. Once the jig mating features are created by the computing device utilizing one or more of the electronic markers on the 2D images, a machining program is generated by the computing device. The machine program may then be provided to a CNC or 3D printing machine to manufacture the jig corresponding to the machining program. The jig is thus matched to the landmarks identified in the series of 2D images of the patient's vertebra. Further, the procedure does not require the generation of a three-dimensional (3D) model of the patient's anatomy to manufacture the customized nature of the jig. Rather, by utilizing one or more mating shapes that contact the vertebra anatomy at particular contact points of the vertebra anatomy corresponding to the identified landmarks in the 2D images, the customization of the jig is achieved. Further, because the procedure does not require the generation of a 3D vertebra model, the customized jigs may be produced more quickly, accurately and efficiently than previous customization methods.

To aid in the description below of the customized MIS spine guides and methods for creating said jigs, a brief discussion of the anatomy of the human spine is now included. As mentioned above, the present disclosure may be applied to any region of a patient's spine. However, for ease of understanding, the discussion herein is limited to particulars of the thoracic and lumbar vertebrae as an example of the spine relating to the present disclosure procedure and apparatus.

Further, it would be desirable to eliminate the full segmentation process and the associated three dimensional anatomical modeling of a vertebra surface, and to replace this approach with data obtained from relatively few MRI, CT or X-ray "slices," as few as, for example, three (3) two-dimensional slices, that permits flexibility in choice of contact points between the vertebra surface and the MIS spine jig that facilitates the placement of the pedicle screw implant or instrument (e.g. drill tap, K-wire, optical tracking, mechanical bone registration, robotics). It would be even more desirable to replace the "full segmentation" procedure, with its thousands of grid points, with a simpler, quicker procedure (minutes instead of hours) that works with as few as about seven (7) contact points between an anatomical surface, such as the posterior spinous process and lamina. Aspects of the present disclosure may involve a "point contact" approach that provides a MIS guide mechanism, which defines a trajectory for an implant or instrument.

FIG. 1 illustrates a posterior view of the patient's spine divided into four regions called the cervical 102, the thoracic 104, the lumbar 106, and the sacrum 108. The cervical vertebrae 102 are numbered from (C1-C7) where C1 is the closest to the skull and C2-C7 proceeding away from the skull and down the spine. Thoracic vertebrae 104 are the longest region of the spine and the most complex. Connecting with the cervical vertebrae 102 above and the lumbar vertebrae 106 below, the thoracic vertebrae 104 runs from the base of the neck down to the abdomen and are the only spine region attached to the rib cage. Thoracic vertebrae 104 are numbered form (T01-T12) where T01 is closes to the neck or C7 and T02-T12 proceeding away from the neck and runs down the spine. The lumbar vertebrae 106, also known as the lower back, consist of five vertebrae labeled L1-L5. The lumbar region of the spine is situated between the thoracic 106 or chest region and the sacrum 108. The lumbar vertebrae 106 are connected by the facet joints, which allow forward and backward extensions, as well as twisting movements of the lower back. The two lowest segments L4-L5 of the lumbar vertebrae 106 carry the most weight and have most movement, making prone to injury. The sacrum 108 is a large triangular bone at the base of the spine that forms by the fusing of sacral vertebrae S1-S5. Sacrum 108 is a complex structure providing support for the spine and accommodation for the spinal nerves. Additional details and features of the thoracic and lumbar vertebrae are discussed below with reference to FIGS. 2-5.

Figure 2:
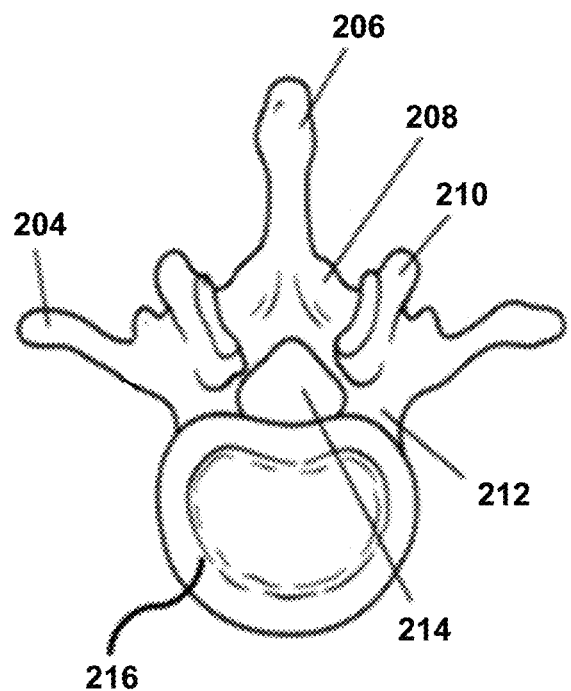
FIG. 2 is an axial view of a lumbar vertebra of a human spine.
Figure 3:
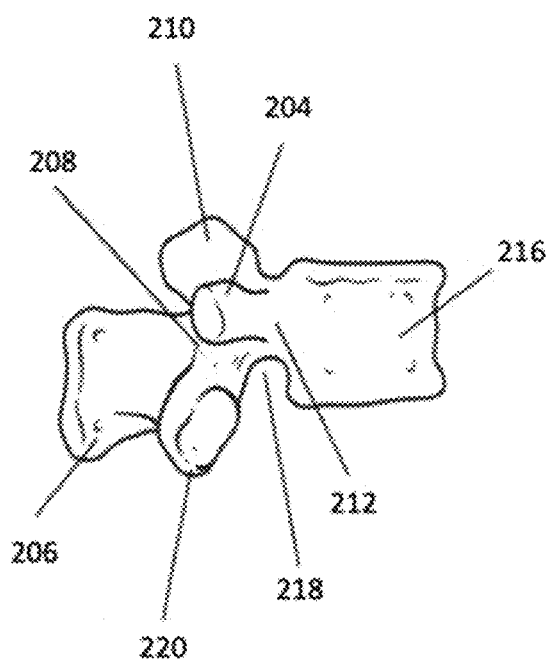
FIG. 3 is a sagittal view of a lumbar vertebra of a human spine.

FIGS. 2-3 are axial and sagittal views, respectively, of a typical lumbar vertebra illustrating the general bony characteristics. As with other vertebrae, each lumbar vertebra consists of a vertebral body 216 and a vertebral arch, consisting of a pair of pedicles 212 and a pair of laminae 208, enclosing the vertebral foramen or canal 214. The pedicles 212 are the strongest bone, directed upward from the upper part of the vertebral body; consequently, the inferior vertebral notches 218 are of considerable depth. The laminae 208 are broad, short and strong. They form the posterior portion of the vertebral arch. The laminae 208 connect the spinous process 206 to the pedicles. The spinous process is thick, broad, and somewhat quadrilateral; it projects backward and ends in a rough, uneven border, thickest below where it is occasionally notched. The superior articular facets 210 are well-defined, projecting respectively upward and downward from the junctions of the pedicles 212 and laminae 208. The facets on the superior articular process 210 are concave; those on the inferior articular facets 220 are convex. The transverse processes 204 are long and slender than the spinous process 206. The transverse processes 204 are horizontal in the upper three lumbar vertebrae (L1-L3) and incline upward in the lower two (L4-L5).

Figure 4:
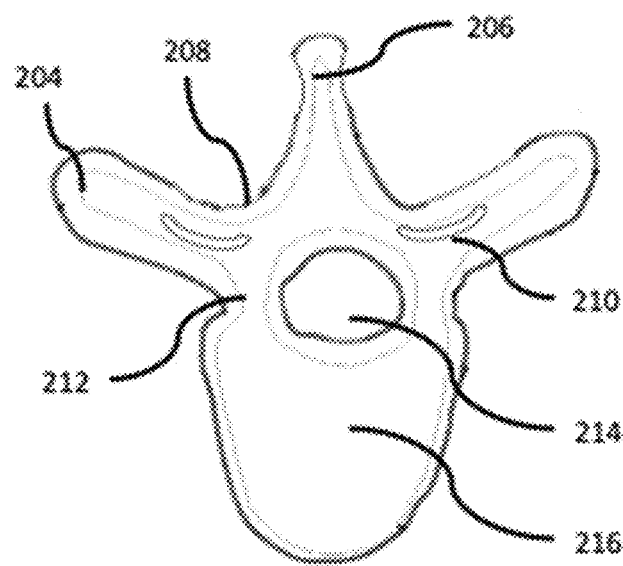
FIG. 4 is an axial view of a thoracic vertebra of a human spine.
Figure 5:
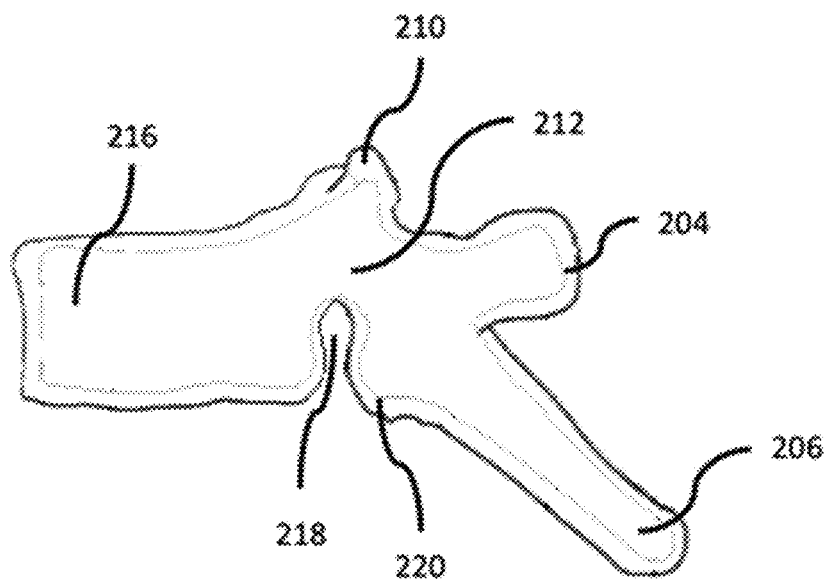
FIG. 5 is a sagittal view of a thoracic vertebra of a human spine.

FIGS. 4-5 are axial and sagittal views respectively of a typical thoracic vertebra illustrating the general bony characteristics. As with other vertebrae, each thoracic vertebra consists of a vertebral body 216 and a vertebral arch, consisting of a pair of pedicles 212 are directed backward and slightly upward, and the inferior vertebral notches 218 are of large size and deeper than any other spine region. The laminae 208 are broad, thick and imbricated, meaning they overlap with subjacent laminae like tiles on a roof to surround and protect the vertebral foramen or canal 214, which is the large opening posterior to the vertebral body. The spinous process 206 is long, somewhat triangular, directed obliquely downward, arising from the laminae 208. The superior articular facets 210 are thin plates of bone projecting upward and inferior articular facets 220 are thin plates of bone projecting downward from the junctions of the pedicles 212 and laminae 208. The transverse processes 204 arise from the arch behind the superior articular processes; they are thick, strong and considerable length, directed obliquely backward and lateral ward. They are situated behind the articular process and are homologous with the ribs.

Figure 6:
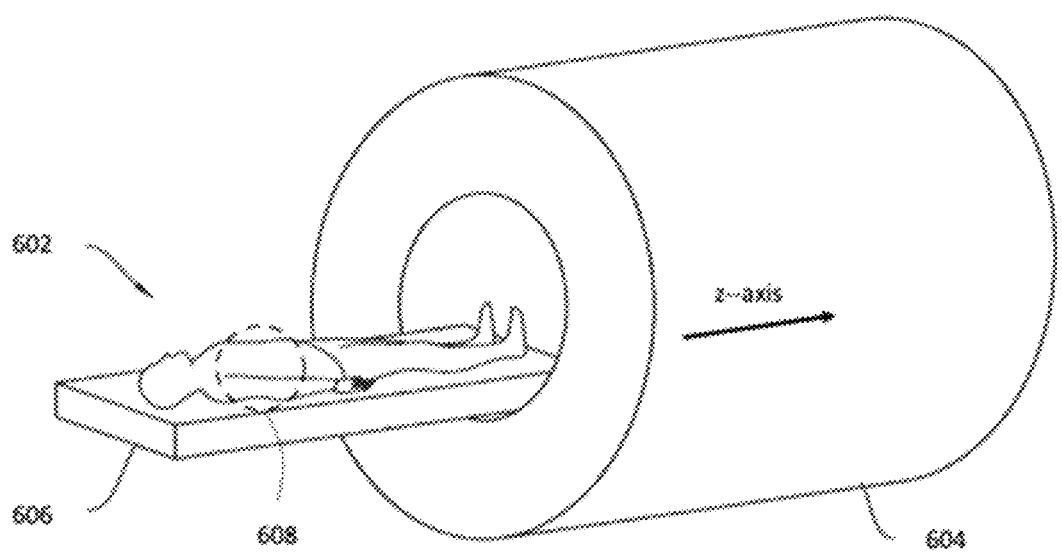
FIG. 6 is an illustration of imaging device to obtain imaging data of a patient's spine.

FIG. 6 illustrates one embodiment for obtaining imaging data of the patient's vertebrae on which the surgical procedure is to be performed. The imaging data of the patient's spine 608 may be obtained from an imaging device 602, such as, computed tomography (CT), magnetic resonance imaging (MRI) or X-ray machine from one or more vertebral segments of the patient's spine undergoing the surgical procedure described in more detail in FIG. 7. In the case of MRI scanning, the patient's spine is scanned in a spine coil to generate a plurality of 2D images to enhance the signal quality of the imaging data received by the imaging device 602. The patient is first positioned on the scanner table 606 and then moved into the bore 604 along the z-axis of the machine coordinate system during the scanning process. Scanning time, image quality and image resolution can vary depending on the scanning parameters, sequence and type of imaging device.

Figure 7:
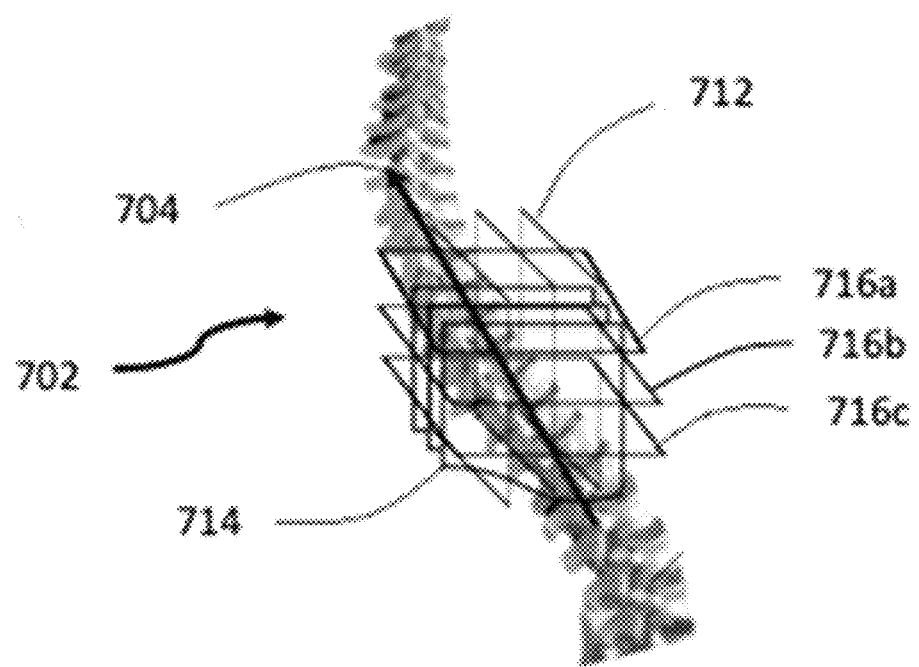
FIG. 7 is an illustration of one embodiment for obtaining 2D images of a patient's vertebrae undergoing a spine procedure.

FIG. 7 illustrates one embodiment of obtaining a series of two-dimensional (2D) images of the patient's vertebrae 702. In one particular embodiment, the patient's spine including all or part of the cervical, thoracic, lumbar and sacrum vertebral segments of interest along the scanner table 606 defined z-axis 704 is scanned using an imaging device 604 illustrated in FIG. 6 to generate a plurality of 2D images (image slices). In one embodiment, the 2D images of the patient's vertebrae include a plurality of 2D image slices taken along a coronal plane 716*a*-716*c*, a plurality of 2D image slices taken along the axial plane 714 and/or a plurality of 2D image slices taken along the sagittal plane 712. In other embodiments, the 2D images may be taken in any combination of coronal, axial and/or sagittal planes or in all 3 planes simultaneously (3D scan). In one embodiment, the MRI spacing for the 2D image slices may range approximately from 1 mm to 4 mm and may vary from aspect to aspect. For example, the 2D image slices between 714*a* and 716*c* may be spaced 2 mm apart, while the sagittal 2D image slices may be spaced 4 mm apart.

Figure 8:
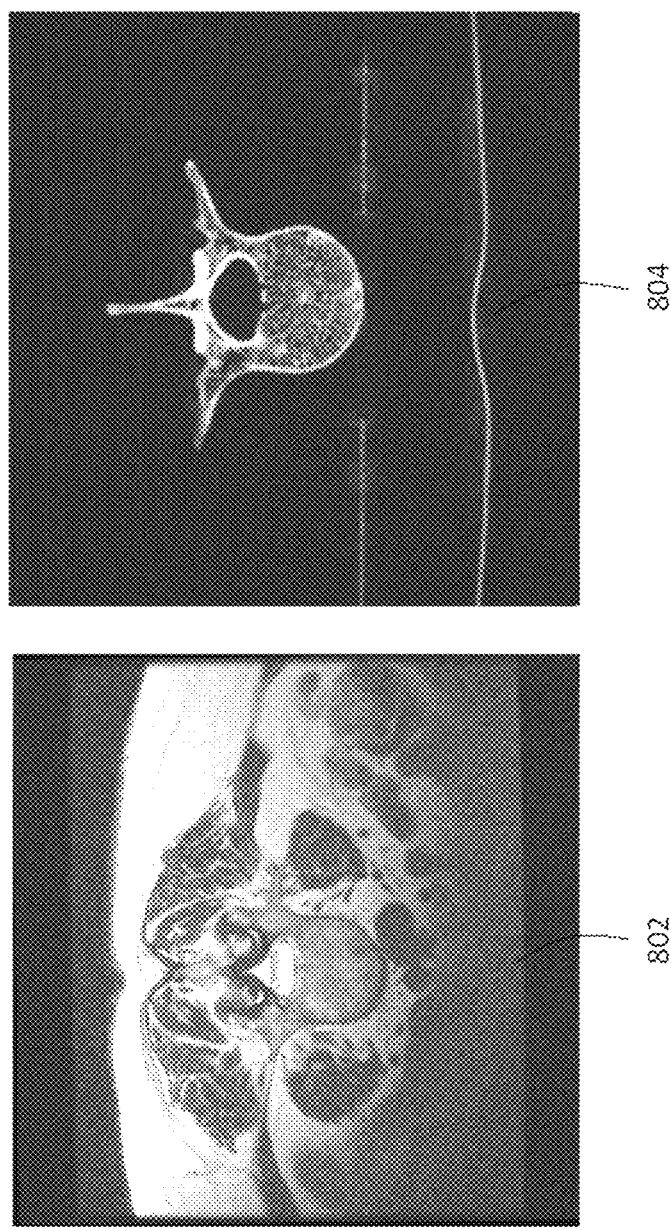
FIG. 8 is a screenshot showing exemplary MRI and CT imaging data in accordance with one embodiment.

While the embodiments herein are discussed in the context of the MRI, in other embodiments the imaging device 604 is via CT, X-ray or other medical imaging methods and systems. For example, FIG. 8 is a screenshot of the patient's lumbar vertebra in axial views comparing an MRI slice image 802 and a CT slice image 804. Further, although it is discussed herein as a scan of the lumbar vertebrae, the 2D images may be obtained for any spine regions or other area of the patient's body, such as images of the patient's skull, hip, rib cage, etc.

Once the 2D images of the patient's vertebrae at issue are obtained, the images may be transmitted to or otherwise provided to a computing device for processing from the imaging device 604. The computing device may receive the images through a wired or wireless network connection from the imaging device 604 in any fashion. In one example, the 2D images may be obtained from the imaging device 604 transmitted to a cloud-based storage device through a network connection accessible by the computing device. The hardware requirements of the computing device are discussed in more detail below with reference to FIG. 33. In particular, the 2D image slices in DICOM format or other suitable digital image formats (JPG, PNG, TIFF, etc.) is a coronal view roughly encompasses all of the transverse processes, posterior spinous process and anterior vertebral body of the vertebrae to undergo the surgical procedure. Although the 2D coronal image slice is referred to for the discussion herein, it should be appreciated that any 2D coronal, axial, sagittal or oblique images may be utilized.

Figure 9A:
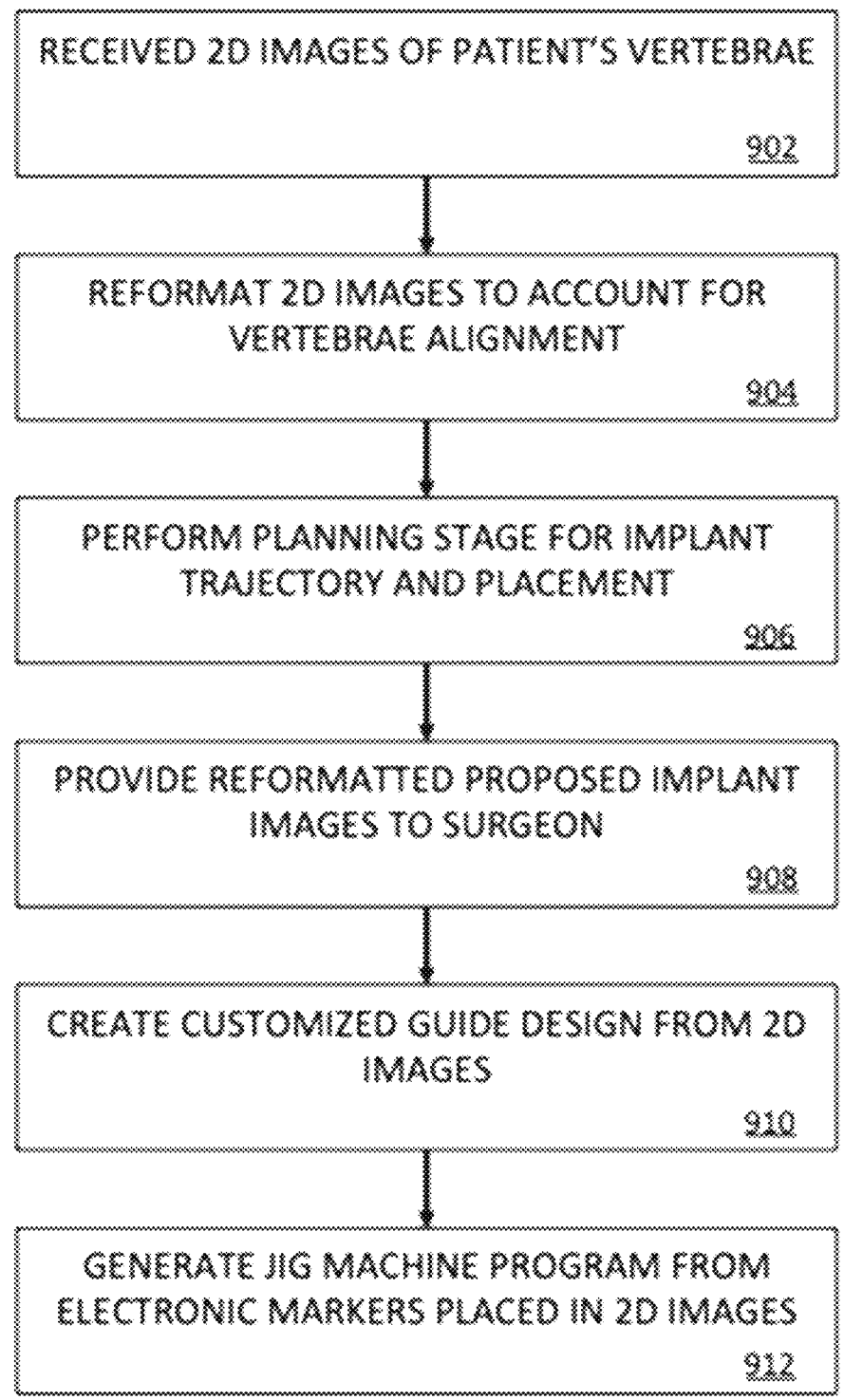
FIG. 9A is a flowchart illustrating a method for creating a customized MIS spine guide from one or more 2D images of patient's vertebrae in accordance with one embodiment.

In general, during a spinal procedure, one or more customized guides may be utilized to aid the surgeon performing aspects of the spinal procedure. For example, the insertion of a spinal screw may occur during the procedure. A customized guide may be utilized to aid the surgeon in the placement and insertion of the screw or other implement into the spinal bone. One method for manufacturing such a customized MIS spine guide is illustrated in the flowchart of FIG. 9A, in particular, the process of receiving a series of 2D images of the patient's vertebrae undergoing the surgical procedure to generating a machine program provided to a CNC (or the like) or 3D printing machine to fabricate a customized MIS spine guide for use in a surgical procedure by the operating surgeon. In general, the operations of the flowchart in FIG. 9A may be performed by an operator of a computing device, the computing device itself, the artificial intelligence software running on the computing device or a combination of the operator, software program and the computing device.

In one embodiment, the operations described below in reference to FIG. 9A may be performed multiple times for the right and left side of the vertebra or different vertebrae that make up a region of the spine. For example, in a two-segment (L1-L2) spinal fusion procedure, the operations of FIG. 9A may be performed four times for images of the left and right sides of patient's lumbar vertebrae L1-L2. The operations may be performed for each vertebra of the spine to account for arthritic or other damage done to the patient's spine. In particular and as explained in more detail below, the operations described herein are utilized to reformat the received 2D images of the patient to approximate true anatomical images of the patient's anatomy. In other words, the images are reformatted to approximate true sagittal, axial, and coronal views of the vertebra. However, due to damage of the vertebra, reformatting of the vertebra to a true anatomical view may be difficult. Thus, the operations utilized to reformat the images may be performed separately on each vertebra.

Further, many of the operations may be performed multiple times. For example, the images may be reformatted as described below any number of times to fine-tune images illustrating the vertebrae in a true anatomical view. Thus, a first iteration of the reformatting may be performed for a first correction of the images closer to a true anatomical view. Additional iterations of the reformatting process may then be performed to fine-tune the images into a global coordinate system that approximates true anatomical views of the patient's vertebrae. Further, the reformatting of each vertebra of the spine may be performed multiple times so that the approximation of the true anatomical view of the images is performed for the different vertebrae of the spine separately. As such, one or more of the operations described below may be performed any number of times to aid in reformatting the received 2D images to approximate a true anatomical image of the vertebral segments of the spine in relation to the surgical procedure.

Beginning in operating 902, a series of 2D image of the patient's vertebrae is received by the computing device generated by an imaging device 602. In one embodiment, the computing device received the 2D images over a network or virtual network from the imaging device 602 or other computing device associated with the imaging device 602. The 2D images may be packaged into a series of images that are available to be viewed through a display of the computing device. Also, as described above, the 2D images of the patient's vertebrae include a plurality of images taken along a coronal plane, an axial plane or a sagittal plane through the vertebrae and/or other regions of the patient's spine, or a combination of coronal, sagittal, axial and/or oblique views. Once the 2D images of the vertebrae are transmitted or otherwise available, the received 2D images may be stored in a computer-readable medium for further processing by the operator or computing device utilizing a software program running on the computing device.

In operation 904, the 2D images may be reformatted to account for vertebrae alignment of the patient by converting the images from a machine-defined coordinate system to another coordinate system by identifying one or more points or landmarks associated with the patient's anatomy that may mate with contact points or surfaces of the customized guide. In general, the reformatting of the 2D images occurs through the placement or location of one or more reference points or lines within the 2D images to reformat the images to true anatomical views. Using one or more 2D images selected, the computing device or an operator using electronic makers (points and lines) may identify the landmarks of the patient's anatomy within the images. Through these marked landmarks (points and reference lines), the computing device can reformat the 2D images into true anatomical views that may be used to create a customized MIS spine guide or viewed by the operating surgeon to approve the surgical plan, as explained in more detail below.

In addition, reformatting the 2D images through the computing device may provide several functions to the overall customized guide creation method. For example, during the reformatting stage unusable or misaligned 2D images of the patient's vertebrae may be noted and/or discarded. This allows for a request for additional images to be taken of the patient's vertebrae early in the jig creation process. In addition, the imaging process may include several irregularities that may affect the effectiveness of the customized guide. For example, during imaging, the patient may be oriented at an angle within the imaging device such that each of the images taken may not align with the imaging device (machine) coordinates. In this example, the resulting images may be misaligned with the global coordinates of the imaging device 602, making the location of the landmarks within the 2D images be similarly off-axis from the true anatomical views or global coordinate system. However, through the reformatting stage described below, one or more of the 2D images may be realigned or reoriented to compensate for the angle in which the patient was placed in the imaging device 602.

In one embodiment, a program executed by the computing device may obtain the 2D images, determine the one or more reference points within the images, reformat the images, and/or identify the landmarks within the 2D images that correspond to contact surfaces of the customized guide, with or without the aid of an operator of the computing device. In another embodiment, one or more of these operations are performed by the operator, while other operations are performed by the computer program. As such, any of the operations and methods described herein may be performed by an operator of the computing device or the computing device itself through hardware, software, or a combination of both hardware and software After reformatting of the images occurs, the operator or computing device may then perform a planning stage on the 2D images, as shown in operation 906. During the planning stage, one or more landmarks on the 2D images of the patient's vertebra are identified and noted with electronic markers on the images in the computing device. In one embodiment, these landmarks are utilized by the computing device to create a reference within the 2D images in which a customized jig may be located in relation to the anatomy contained within the 2D images. For example, during the planning stage, the operator or a surgeon may indicate the initial or default pedicle screw or instrument trajectory based on the 2D images of the patient's vertebra. As described in more detail below, the planning stage provides several reference points, lines or landmarks in the 2D images to the computing device that may be utilized by the computing device in creating a customized MIS jig. Also discussed below, the planning stage may be performed for each vertebra of the spine. This is due to the reformatting of the 2D images operation occurring on each vertebral segment of the patient's spine. In other words, the lumbar vertebra L1 may be reformatted in a particular orientation while the lumbar vertebra L2 is reformatted in another orientation due to disc damage and different pedicle placement trajectory for each vertebra. As such, the planning operations may be performed for the various portions of the spine and different sides (left or right) independently that undergo the reformatting operation.

Figure 9B:
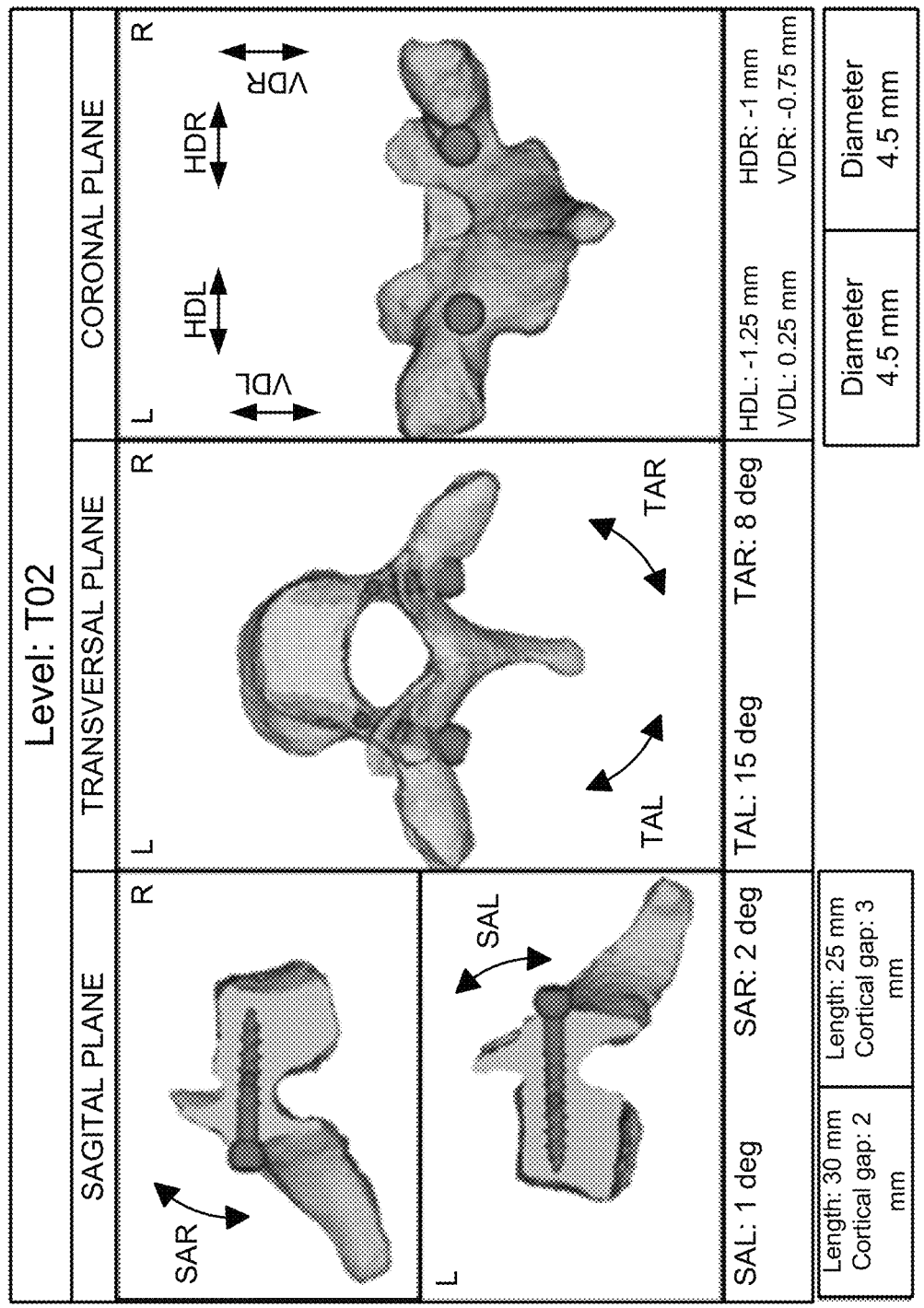
FIG. 9B is a screenshot of display of a patient's thoracic vertebra (T02) planning images shown in true anatomical views (Sagittal, Transversal and Coronal Planes) in accordance with one embodiment.

In operation 908, a screenshot of the reformatted 2D images may be captured by the computing device and a stencil of the pedicle screw, implant, or instrument may be superimposed on the reformatted 2D images. For example, the reformatted thoracic T2 images may be captured and a generic pedicle screw with a certain length and diameter may be superimposed on the reformatted thoracic 2D images. One example of the reformatted 2D images and pedicle screw implant stencil for a patient's thoracic T02 is illustrated in FIG. 9B. Also, the reformatted 2D images and pedicle screw stencils such as those shown in FIG. 9B may be provided to the operating surgeon for approval or making adjustments based on the individual patient. In particular, the true anatomical images may be transmitted from the computing device to the surgeon for review via a network site or a mobile device. In one embodiment, the 2D images are available through a website or an app on the mobile device for review by the surgeon. For example, the surgeon may verify that the pedicle screw or instrument trajectory, size (diameter and length) and placement of the pedicle screws are located in the center of the pedicle within the 5-walls of the bone. In general, the operating surgeon when evaluating the proposed implant or instrument trajectory on the reformatted 2D images may utilize any criteria, patient health history or surgical technique.

Upon approval by the surgeon, the design of the jig may occur. In one embodiment, the surgeon may visually determine the proper trajectory and placement of the proposed pedicle screws or instruments on the reformatted 2D images of the patient's vertebra and indicate an approval with an input device to a computer or mobile device on which the images are being reviewed. The provided reformatted images may also include specific measurements of the pedicle screw implant or instruments, such as length, diameter, cortical gap, angle and position of the implant or instrument, and the like. Also, the provided reformatted 2D images may include a true sagittal image for the Right and Left side of the vertebra, a true coronal image of the vertebra and a true axial or transversal image for each vertebra to undergo the surgical procedure.

Figure 25A:
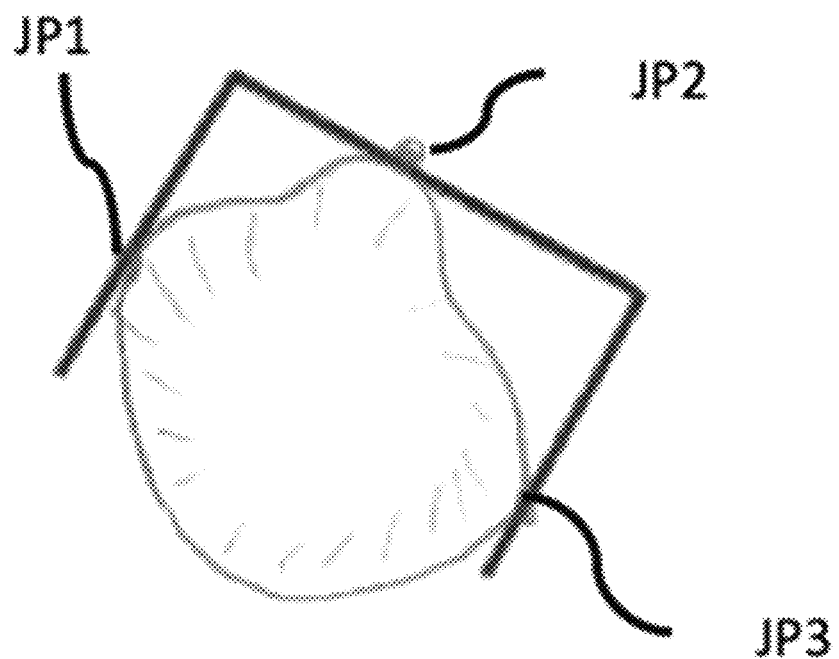
FIGS. 25A and 25B illustrate one and two-dimensional, open and closed, linear and curvilinear shapes that can be used as mating features in determining the contact points for creating the embodiments.
Figure 25B:
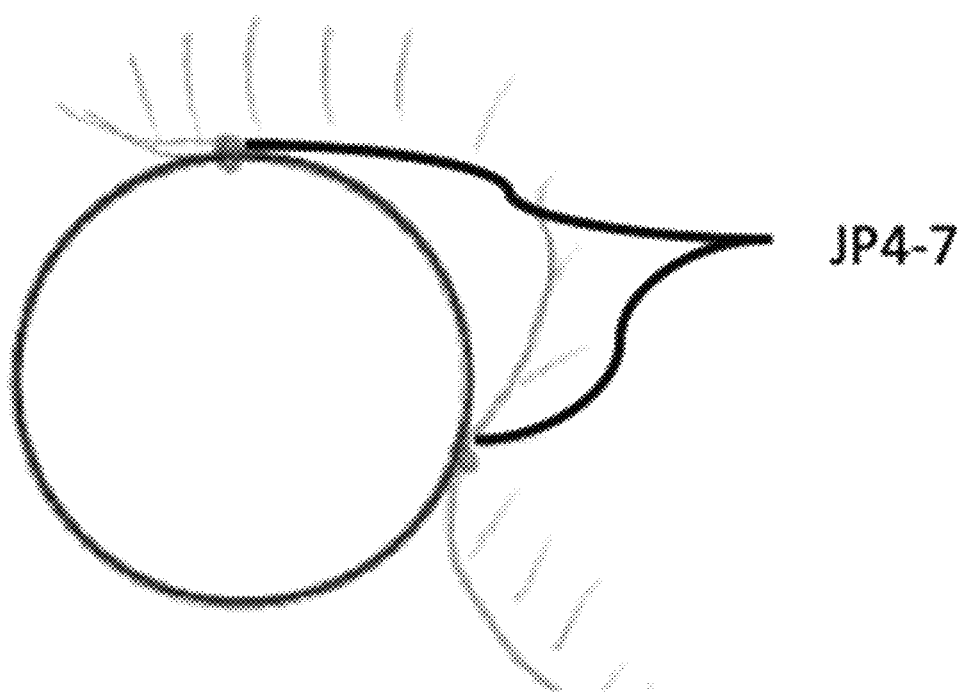

In operation 910, the operator or computing device may then perform a jig design stage on the 2D images. During the jig design stage, one or more electronic markers or shapes are placed on or otherwise associated with one or more of the reformatted 2D images of the patient's vertebra. It should be noted that reference and discussion of 2D images in this invention may refer to either the original 2D images of the patient's vertebra, the reformatted images of the patient's vertebra as described above, or a combination of both the original and the reformatted images. In one example, the electronic shapes correspond to contact shapes of the customized jigs for the vertebra is illustrated in FIGS. 25A-25B. Thus, the electronic shapes may be placed by the operator or computing device in the 2D image in locations similar to mating locations on the patient's vertebra for the customized jig. In particular, the jig design features identified in the 2D images are translated into the machine program or computational information to create a jig that is customized to the particular vertebra shown in the 2D images This computational information may be provided to a milling or 3D printing device, such as a computer numerical control (CNC) milling or 3D printing device in operation 912, to create the customized MIS spine jig for the surgical procedure based at least on the computational information provided to the milling or 3D printing device. In general, a CNC machine or 3D printing device is operated by programmed commands included in a program or list of commands to remove or add material or create an apparatus based on the instructions provided in the commands. Thus, in this example, CNC milling machines translate the commands into control signals of a cutting device to mill a jig out of a jig blank according to the provided information. As pertaining to the method of FIG. 9A, the computational information generated by the computing device associated with the electronic markers in the 2D images are utilized to generate the series of commands to operate the CNC milling or 3D printing machine. Thus, a customized spine jig is created by providing the milling or cut-file program that includes information concerning the electronic markers in the 2D images and a jig or guide blank to the CNC machine so that the machine mills or otherwise creates the customized jig based on the instructions of the milling program. In this manner, 2D images of a joint may be utilized to create a customized spine jig for use in surgical procedures to stabilize to vertebrae of a patient.

Figure 10:
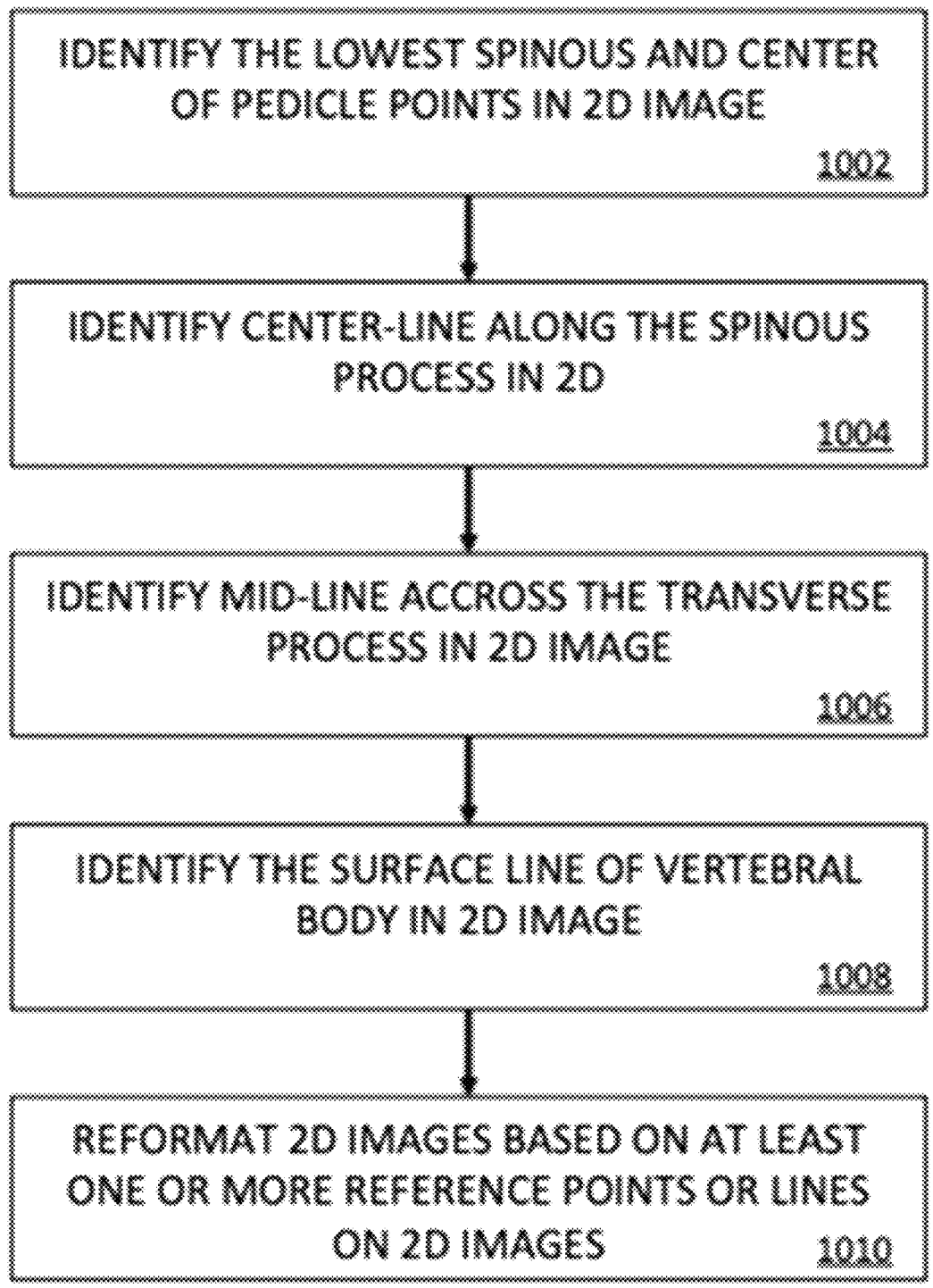
FIG. 10 is a flowchart illustrating a method for reformatting a series of 2D images of patient's vertebra to true anatomical views or global coordinate system in accordance with one embodiment.

As mentioned above, a reformatting of the 2D images of the patient's vertebra may be conducted to reorient in three dimensions and verify the quality of the images. FIG. 10 is a flowchart illustrating a method for reformatting a series of 2D images of a patient's vertebrae to adjust the images from an image machine-determined coordinate system to an approximate true anatomical or global coordinate system. Additionally, the flowchart of FIG. 10 allows an operator or the computing device to identify and reject a series of 2D images that may not be accurate or applicable to the process of creating the customized spine jig. The operations detailed in FIG. 10 may be performed as operation 904 described above. As such, the operations may be performed by an operator of a computing device or the computing device itself through which the 2D images are available for viewing, alterable, and available for placing electronic markers within the images.

Beginning in operation 1002, the computing device may identify the approximate most posterior point of the patient's spinous process in one of the 2D images. In one example, the set of 2D images provided to the computing device are axial views of a patient's vertebra. In other examples, however, the 2D images may be sagittal or axial views. As explained above, the 2D images may be a set of 2D images obtained through an imaging device 602 as the device takes a series of slice images of the vertebrae. Thus, any number of coronal, axial or sagittal images may be present in the set of 2D images from which the clearest or best fit image may be selected by the operator or computing device by tabbing through the set of images. In particular, the operator or computing device tabs through the series of images to determine visually a particular 2D image until a clear image of the spinous process, and in particular the lowest instance of the spinous process, is visible in the image. In one embodiment, the selected 2D image 1102 includes the widest instance of the pedicle bone in the 2D image slice.

Figure 11:
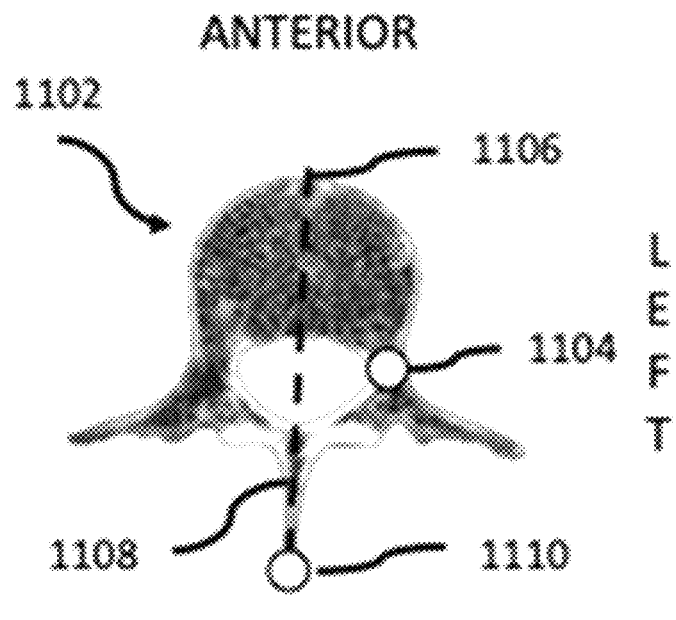
FIG. 11 is a screenshot of patient's vertebra in axial view with spinous process, mid-line of spinous process and center of pedicle for 2D reformatting.

Once a 2D image 1102 is selected, the computing device (or operator utilizing an input device such as a mouse or a keyboard) locates and electronically marks the spinous process on the selected 2D image. In particular, the operator attempts to locate and electronically mark the lowest instance or most posterior point of the spinous process in the selected 2D image. In the example of FIG. 11, the electronic marking of the lowest instance of spinous process 1110 is then stored in the computing device and used in operation 1010 to reformat the 2D images. It is not necessary that the exact most posterior point of the spinous process 1110 be indicated. Rather, the selection of the point can be approximate.

Continuing from the previous operation above, the center point of the pedicle on the selected 2D image is then selected by the computing device or the operator. In particular, the center point of the pedicle 1104 is located, which has a cylindrically shape. In the example of FIG. 11, the electronic markings of the center point of the left pedicle 1104 is selected and then stored in the computing device to establish a global coordinate system for the series of 2D images as explained in more detail below. As mentioned above, it is not necessary that the operator select exactly on the center point of the left pedicle 1104. Rather, the selection of the point can be approximate. In addition, the operator or computing device can locate the center point of the right pedicle using similar operation discussed above.

In operation 1004, the operator or computing device selects a 2D image from the set of images and identifies the mid-line of the spinous process. In particular, the Gaussian like shape of the spinous process may be observed in one of a series of axial 2D images. Thus, the computing system may tab through the various axial 2D images of the vertebra and select a 2D image with the lowest instance of the spinous process. The selected image may be the same image slice 1102 in the previous operation 1002. Once a 2D image is selected, the centerline of the spinous process from the point 1110 to the highest point or most anterior point of the vertebral body 1106 may be located and electronically marked. An example of the electronic marker located at the mid-line of the spinous process 1108 is shown in the 2D axial image of the vertebra in the screenshot 1102 of FIG. 11. The electronic marking of the centerline 1108 is then stored in the computing device to reorient the 2D images. The location of the mid-line 1108 and posterior of the spinous process 1110 in the 2D images may also aid the computing device in determining the orientation and left and right side of the patient's vertebra in relation to the 2D images.

Figure 12:
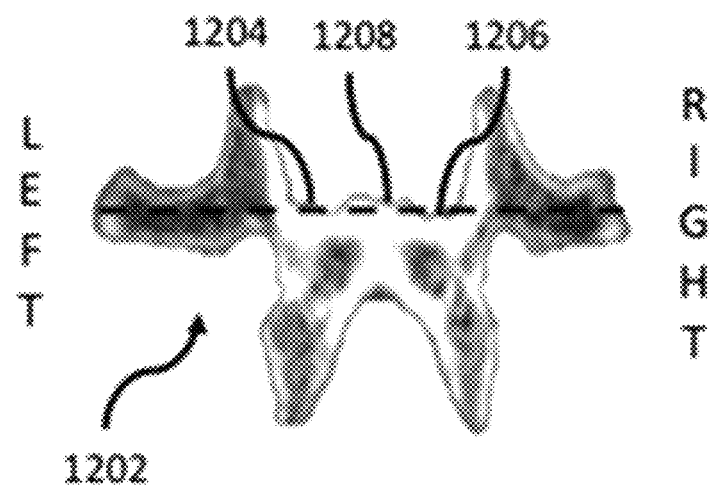
FIG. 12 is a screenshot of patient's vertebra in coronal view with the mid-line of transverse process identified for 2D reformatting.

Continuing the reformatting of the 2D images, the operator or computing device identifies a mid-line across the transverse process in operation 1006. Similar to the discussion above, the computing device tabs through the various 2D images of the patient's vertebra and selects one or more coronal images showing the transverse processes 204 patient's vertebra. Once a 2D image is selected, the mid-line 1208 across transverse processes in the image may be located and electronically marked using the superior edges 1204 and 1206 of vertebral foramen or canal 214 as visual reference. FIG. 12 is an example of the electronic marker identifying the mid-line 1208 on the transverse processes in the selected 2D coronal image 1202 of the patient's vertebra. As should be appreciated, the mid-line 1208 may indicate the damage or curvature of the patient's spine in the posterior or coronal view during the imaging process. The electronic marking of the mid-line on the transverse process 1208 is then stored in the computing device as a marker related to the vertebra for orienting the 2D images as described below.

Figure 13:
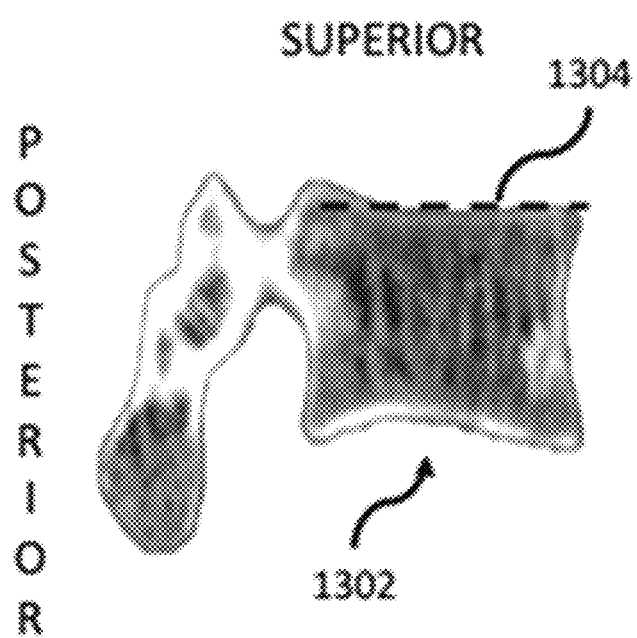
FIG. 13 is a screenshot of patient's vertebra in sagittal view with the superior vertebral body surface line identified for 2D reformatting.

In operation 1008, the operator or computing device identifies superior vertebral body surface line in at least one of the 2D images. To determine the superior vertebral body surface line 1304, the computing device may tab through the set of sagittal 2D images of the patient's vertebra and select one or more images to identify points or lines on the image. In particular, the operator or computing device identifies a 2D image that includes a nearly straight cortical bone feature on the superior vertebral body. An electronically drawn line along the superior vertebral body surface may be identified or included in the 2D image. As an example, the identification of the superior vertebral body surface line 1304 is shown in the 2D sagittal image 1302 of FIG. 13. In general, the vertebral body surface line 1304 follows the nearly straight cortical bone feature of the vertebra described above. In this manner, a line that indicates the orientation of the superior vertebral body surface is represented on the selected 2D image. As should be appreciated, the superior vertebral body surface line 1304 may indicate the curvature of the patient's spine during the imaging process. This line may be stored in the computing device for re-orienting the 2D images as described below.

In operation 1010, the computing device may utilize one or more of the electronic markers, points and/or lines to reformat the series of 2D images along a coordinate system that more closely approximates a true anatomical view of the patient. In general, the reformatting of the 2D images may include orientation of the images and/or extrapolation of the data between image slices. In this manner, the images are reformatted in three-dimensions to approximate the true anatomical coordinate system. For example, based on the mid-line of the spinous process 1108 and the mid-line of the transverse processes 1208, the computing device can determine the alignment of the patient's vertebrae placed on the scanning table 606 thereby adjusting the angle on each of the generated 2D image slices until a true anatomical or global coordinate system. In addition, the computing device can determine the location of the left and right side of the vertebrae based on the location of the mid-line of the spinous process 1108. Thus, from the information entered into the computing device, each of the 2D images in the series may be reformatted to account for angle of images obtained during imaging of the patient's vertebrae. In general, any of the reference points and lines identified on the 2D images may be considered by the computing device when reformatting the 2D images.

As discussed above, a global coordinate system can be established using the 2D reformatted images, which includes an x-axis, y-axis, and a z-axis. As shown in the example in FIG. 15A, a global coordinate system 1512 of the patient's left lumbar is illustrated. Further, the x-axis and y-axis of the global coordinate system 1512 may be oriented in a plane that is transverse or perpendicular to the z-axis. As should be appreciated, the global coordinate system 1512 is but one system that may be used in the present disclosure. In general, the global coordinate system 1512 may lie in any orientation in relation to the 2D images.

Figure 14:
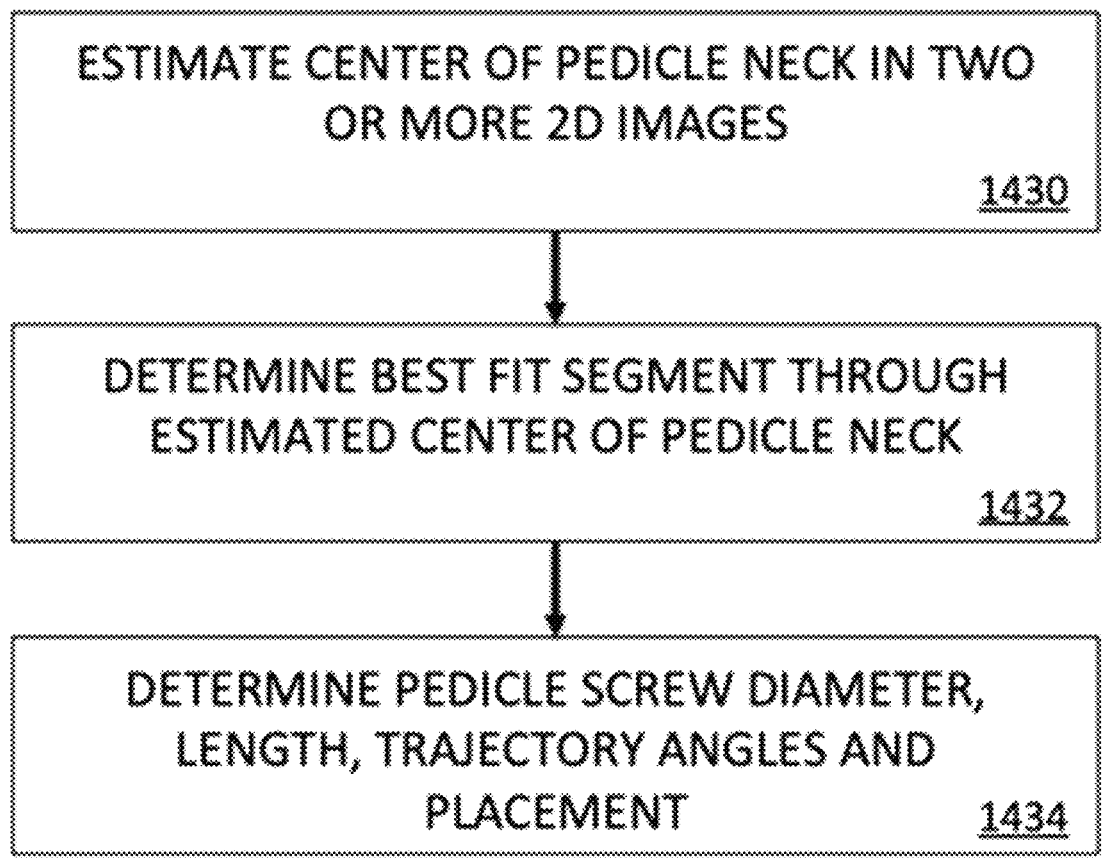
FIG. 14 is a flowchart illustrating a method for determining the center axis of the pedicle of the patient's vertebra to establish an implant or instrument trajectory in accordance with one embodiment.
Figure 15A:
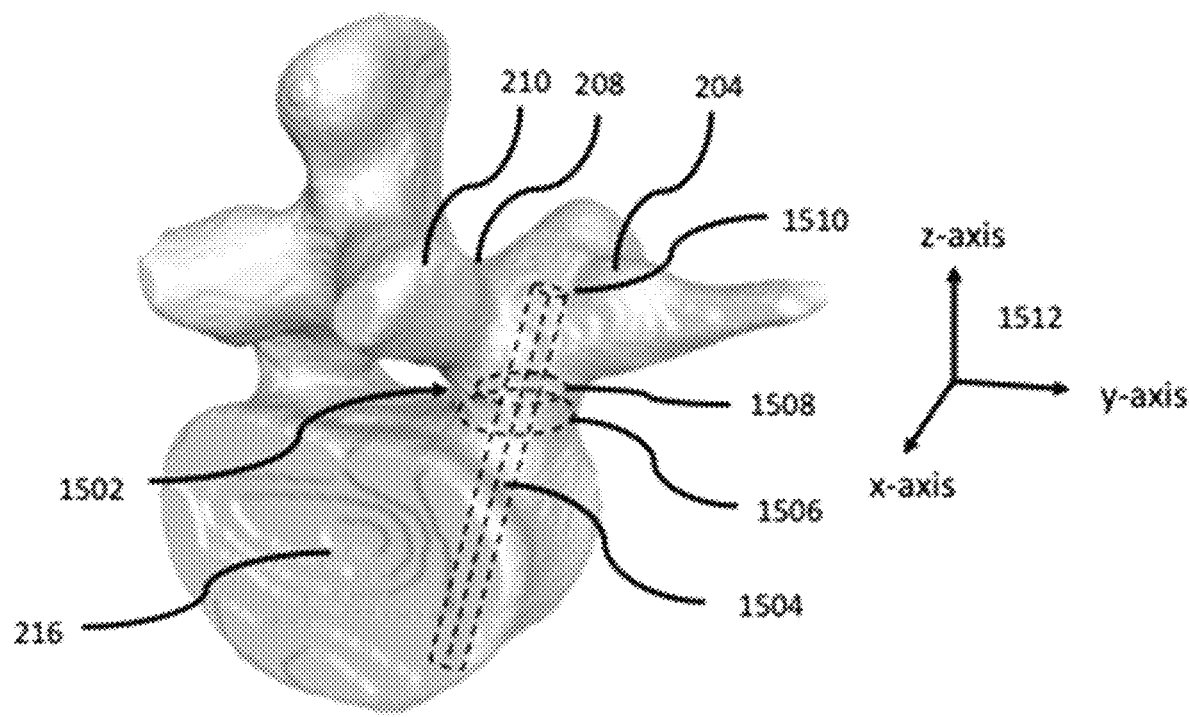
FIG. 15A is a perspective illustration of patient's vertebra with center-axis of pedicle and screw center identified in the global coordinate system using two or more 2D slice images.
Figure 15B:
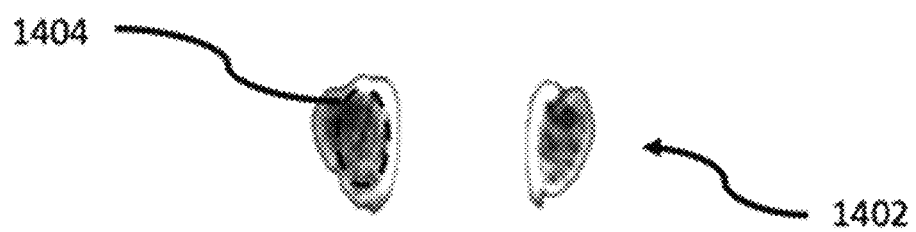
FIGS. 15B-15D are illustrations of patient's vertebra in coronal views with the embodiments with the pedicle and screw centers identified using an oval or circular shape.
Figure 15C:
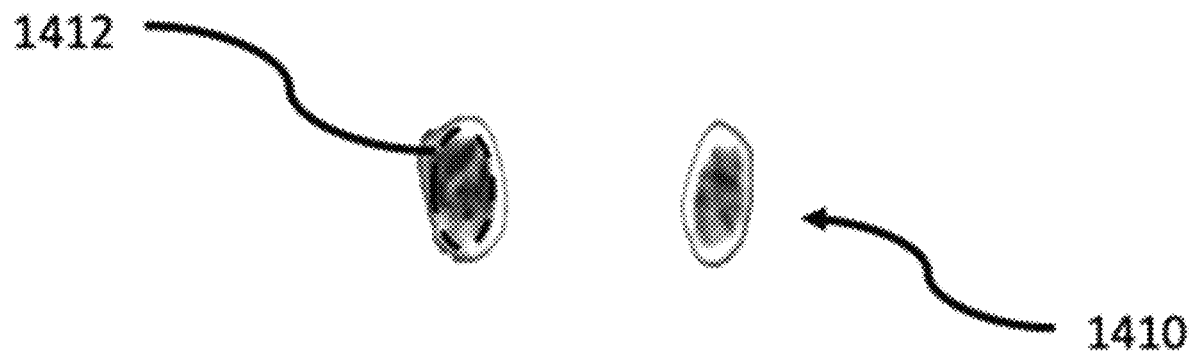

With the set of 2D images reformatted, the computing device may determine an approximate angle and placement of a pedicle screw. In particular, FIG. 14 is a flowchart illustrating a method for determining the center axis of the pedicle of the patient's vertebra to establish an implant or instrument trajectory in accordance with one embodiment. Beginning in operation 1430, the computing device may estimate the center coordinates of the pedicle in two or more reformatted 2D images of the patient's vertebra. As illustrated in FIG. 15A, portions of the pedicle 1502 may be illustrated in one or more image slices. That is, the pedicle 1502 may be a collection of the 2D image slices of the patient's vertebra corresponding to portions of the patient's vertebra, as provided in the received 2D images. In one particular embodiment shown in FIG. 15, the computing device may utilize a sequence of approximately parallel coronal 2D images 1508 and 1506, spaced apart along the z-axis of the global coordinate system 1512. As should be appreciated, however, it is not required that the images be along the z-axis, but may be oriented in any manner in the coordinate system 1512.

Viewed along the z-axis, the selected 2D images of the pedicle form a general oval-shape, representing a cross-section view of the pedicle 1502. For example, FIGS.

15B-15C includes two such 2D reformatted coronal image slices through the pedicle 1502 with corresponding cross-section images 1402 and 1410. Once the cross-section images 1420 and 1410 are selected, the computing device may then estimate a center of the oval in the selected images.

Also included in FIG. 15A is a center-axis (CA) 1504. In one particular embodiment, the z-axis coincides with, or is approximately parallel to, the center axis (CA) 1504. As such, the computing device may determine the CA 1504 directly from the images, or an approximation of the CA 1504 may be provided to the computing device, such as from a user of the device. In one specific example, the user (operator or surgeon during planning stage) may provide a center axis reference line in one or more of the images that approximates the CA 1504. As discussed in more detail below, the computing device may also determine the center-axis 1504 through an analysis of the cross section images 1508 and 1506 of the patient's pedicle 1502 and cross section of the implant or instrument 1510 at the vertebral surface chosen by the operator or computing device. For example, FIG. 15D includes one such 2D reformatted coronal image slice of the upper vertebral body with corresponding cross-section image 1420 and cross section of the implant or instrument 1422 chosen by the operator or computing device.

Figure 15D:
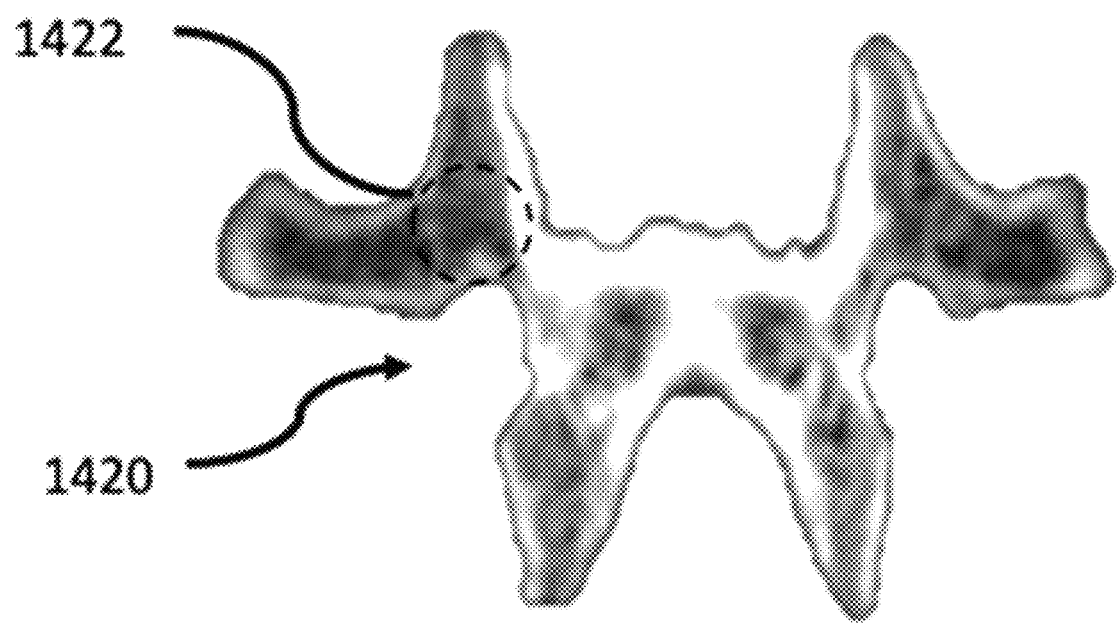
Figure 16:
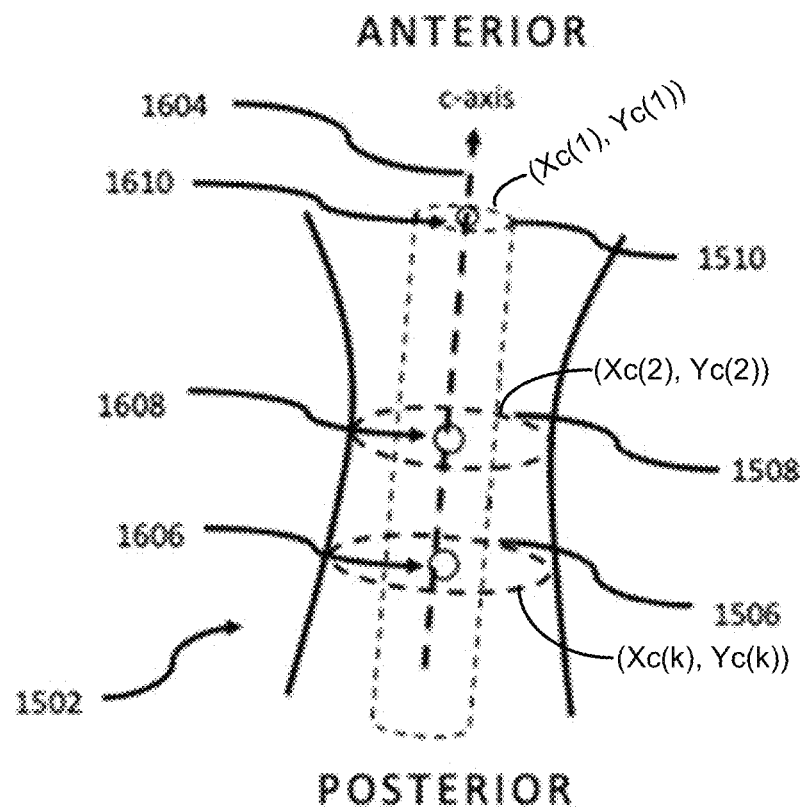
FIG. 16 is a perspective illustration of a pedicle neck providing a best-fit line through or near the center axis of the pedicle and screw center.

As shown in FIG. 16, the cross-section segment 1510 and cross-section segment 1508 are separated along the center-axis 1504. In general, the distance between the images may be any distance along the z-axis. For example, FIG. 16 is a perspective illustration of the left pedicle 1502 of FIG. 15A, including image slice 1510 of the implant or instrument and image slices 1508 and 1506 through the pedicle. As mentioned above, slices through the pedicle 1502 provides a mostly oval-shape and while the implant or instrument cross section provides mostly a circular-shape as shown in FIG. 15D when viewed along the z-axis of the global coordinate system 1512. Thus, image slice 1510 includes estimated center point 1610, image slice 1508 includes estimated center point 1608 and image slice 1506 includes estimated center point 1606. Further, the computing device may determine a coordinate in the coordinate system associated with each estimated center point, such that center point 1610 may correspond to coordinate point (Xc(1), Yc(1)) and center point 1608 may correspond to coordinate point (Xc(2), YcC2)). Further, additional image slices 1506 and center points 1606 (with associated coordinate points ((Xc(k), Yc(k)) may be determined by the computing device.

In one particular embodiment, a sequence of two-dimensional coordinate (xm(k),ym(k)) (where m=1, . . . , M) of spaced apart locations on each oval (where k=1, . . . , K) is measured, and coordinates (xc(k),yc(k)) of geometric center for each oval are estimated as (xc(k),yc(k))=Sum(xm(k),ym(k)/M;

Where m=1, . . . , M. These points may then be assumed to be the centers of the selected image slices along the center-axis 1604 by the computing device.

Once the centers of the image slices 1510, 1508 through the pedicle 1502 are estimated, the computing device may determine a best-fit linear segment adjacent to or near the estimated image slice centers in operation 1432 of the method of FIG. 14. For example, one best-fit linear segment is shown in FIG. 16 for the image slices 1510, 1508 and 1506 through the pedicle 1502. In general, the best-fit linear segment 1604 may be determined by the computing device by minimizing an error function that provides a measure of an error between each of the center coordinate locations and the coordinates of the best fit linear segment as the segment passes through the associated image slice. In this manner, the best-fit linear segment 1604 is created that passes through or near the center coordinates 1606, 1608, and 1610 of the image slices along the pedicle 1502. In this manner, the best-fit linear segment 1604 is created that passes through or near the center coordinates 1608-1610 of the image slices along the pedicle 1502. In one embodiment, the computing device may utilize the best-fit linear segment 1604 as a screw-axis (SA) line 1604 through the pedicle 1502.

Figure 17:
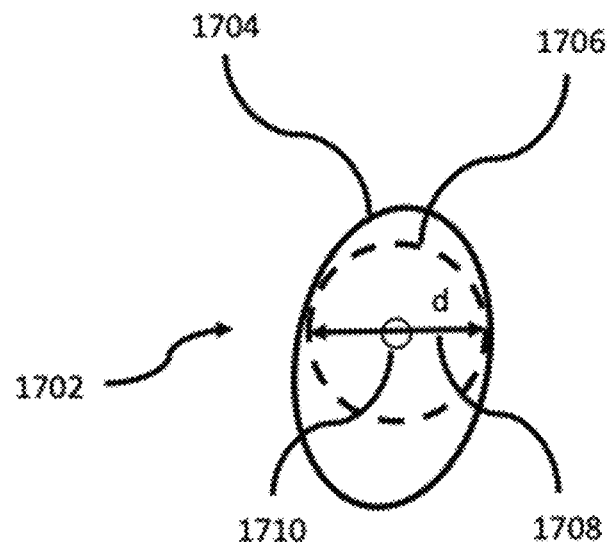
FIG. 17 is an illustration of the coronal view of patient's pedicle providing the center point of the center-axis and screw diameter superimposed on the 2D slice image of pedicle.

In operation 1434, the computing device may then calculate the trajectory angles, diameter, and lengths of the pedicle screw or instrument. As discussed above, the center point of the pedicle 1104 in FIG. 11 is identified in the axial image slice 1102 by the computing device or operator and stored in the computing device. As shown in FIG. 17, the corresponding 2D coronal slice 1702 of pedicle center point 1104 in the axial image may be utilized as one of the cross-section image of the pedicle 1704 with best-fit linear segment 1604 at center point 1710. The pedicle screw or instrument diameter is then calculated as the shortest distance of the oval shape pedicle from the best-fit linear segment center point 1710. Alternatively a circle shape can be superimposed over the 2D coronal slice 1702 containing the oval-shape pedicle 1704, the computing device or operator can adjust the screw diameter (d) 1708 until the circumference is within the cortical bone boundary of the pedicle. In general, the diameter of the pedicle screw or instrument 1706 may be the same or smaller than the shortest distance of the oval-shape pedicle from the center of the screw-axis 1710. As discussed above, the pedicle screw or instrument 1706 diameter (d) 1708 is either calculated by the computing device or chosen by the operator from a standard implant or instrument database.

Figure 18A:
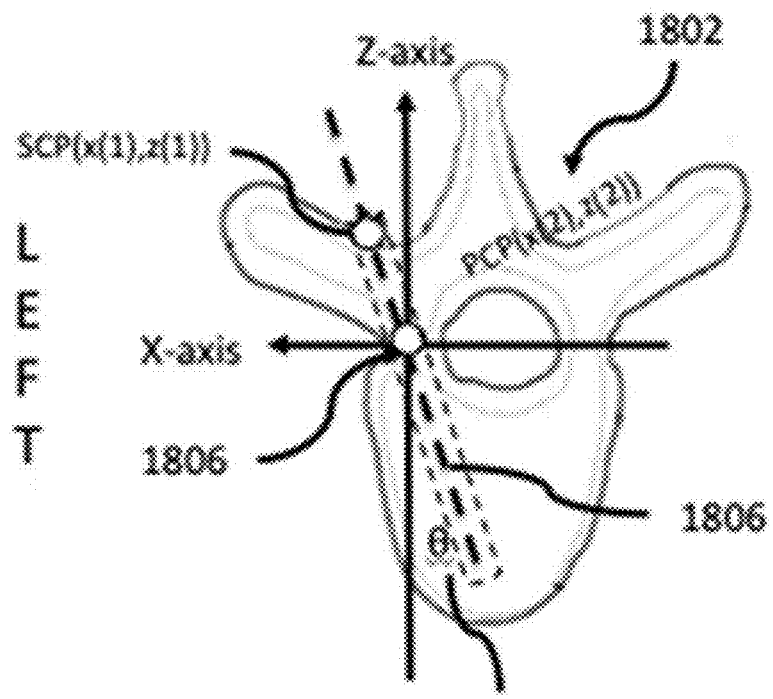
FIG. 18A is an illustration of the axial view of patient's vertebra providing the pedicle center point and angle of the screw-axis relative to the (x axis and z axis) in 2D coordinate system.

Next, the computing device may calculate the trajectory angles of the pedicle screw or instrument using the best-fit screw center point (SCP) 1610 and pedicle center point (PCP) 1608 discussed above. In order to present the pedicle screw or instrument trajectory in true anatomical views, three orthogonal images selected based on the pedicle center point PCP 1608 shown in FIGS. 18A, 18B, and 18C reference. For example, FIG. 18A is an axial slice image 1802 of the patient's vertebra using the PCP in the global coordinate system as the selected slice. For example in FIG. 18A, the x-z axes coordinate system consists of screw center point SCP(x(1),z(1)) and pedicle center point PCP(x(2),z(2)) along with the best-fit center-axis 1806. To calculate the trajectory angle (Θ) relative to the z-axis, the following equation is used:

Θ=tan$^{-1}$(z(2)−z(1))/(x(2)−x(1));

where center point PCP=(x(1),z(1)) and screw center point SCP=(x(2),z(2)).

Figure 18B:
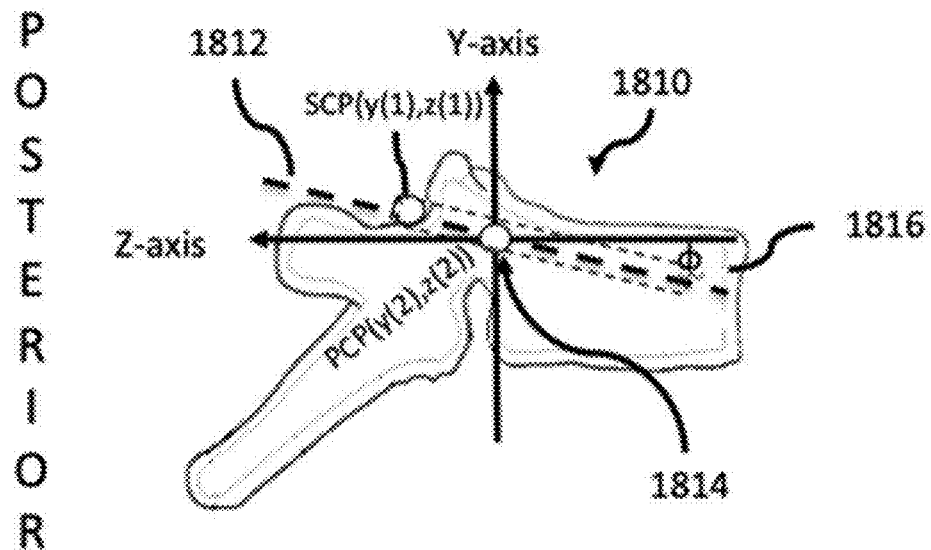
FIG. 18B is an illustration of the sagittal view of patient's vertebra providing the pedicle center point and angle of the screw-axis relative to the (y axis and z axis) in 2D coordinate system.

In one embodiment, as shown in FIG. 18B, a sagittal slice image 1810 of the patient's vertebra using the PCP 1608 as the selected reference point in y-z axes coordinate system. Displayed on the sagittal slice image 1812 are the screw center point SCP(y(1),z(1)) and PCP(y(2),z(2)). To calculate the trajectory angle (φ) relative to the z-axis, the following equation is used:

φ=tan$^{-1}$(z(2)−z(1))/(y(2)−y(1));

where center point PCP=(y(1),z(1)) and screw center point SCP=(y(2),z(2)).

Figure 18C:
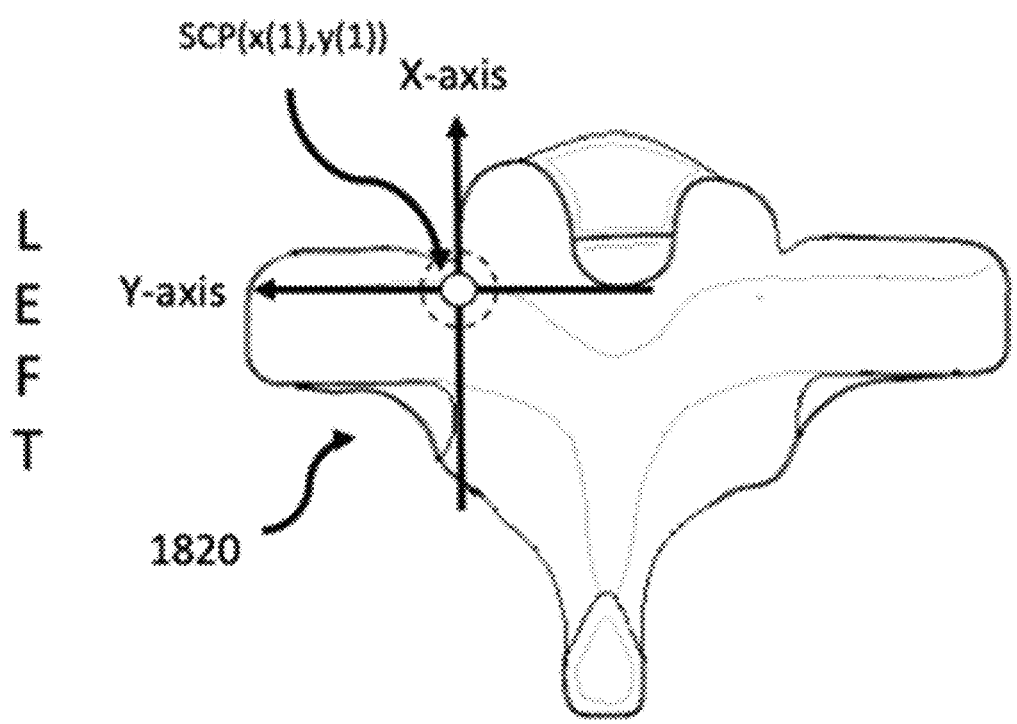
FIG. 18C is an illustration of the coronal view of patient's vertebra providing the pedicle entry point relative to the (x axis and y axis) in 2D coordinate system.

In another embodiment in FIG. 18C, a 2D coronal slice image 1820 of the patient's vertebra using the SCP(x(1),y(1)

in the x-y axes coordinate system is displayed. In general, trajectory angles (Θ, φ) can be calculated and displayed using any 2D reformatted images in the axial, coronal and sagittal plane using the SCP(x(1),y(1),z(1)) and screw-axis defined in the global coordinate system.

The "point contact" approach described herein relies on a small number (e.g., five or fewer) of spaced apart two-dimensional MRI, CT or X-ray images or "slices" of the vertebra anatomical surface, with each slice containing or illuminating one, two, or possibly more contact points between the vertebra anatomical surface and the MIS spine guide or jig that helps define an implant or instrument trajectory for pedicle. Using this approach, more than one jig contact point may be defined for a slice so that some jig contact points may be co-planar relative to the MRI or CT slice and or relative to each other. The approaches discussed herein may have several advantages, including but not limited to: (1) the number of MRI or CT slices actually formed and used is quite small (e.g., about three) and represents about 5-10 percent of the total volume of the portion of the anatomy component of interest; (2) the number of contact points and associated coordinates needed for position stability of the jig is also small (e.g., about 7 or less, as compared with hundreds to thousands for a full segmentation approach); (3) the "design time" required to determine relevant component dimensions and coordinates of the contact points on the anatomical surface is estimated to be no more than 10 minutes and should decrease further as one accumulates experience in the operational process; (4) it is anticipated that this "point contact" approach will permit semi-custom design and fabrication of the implants and associated tools; and/or (5) provides some flexibility for the spine surgeon to exercise creativity, experience and judgment in choices and modifications of some of the dimensions and angular orientations.

Figure 19:
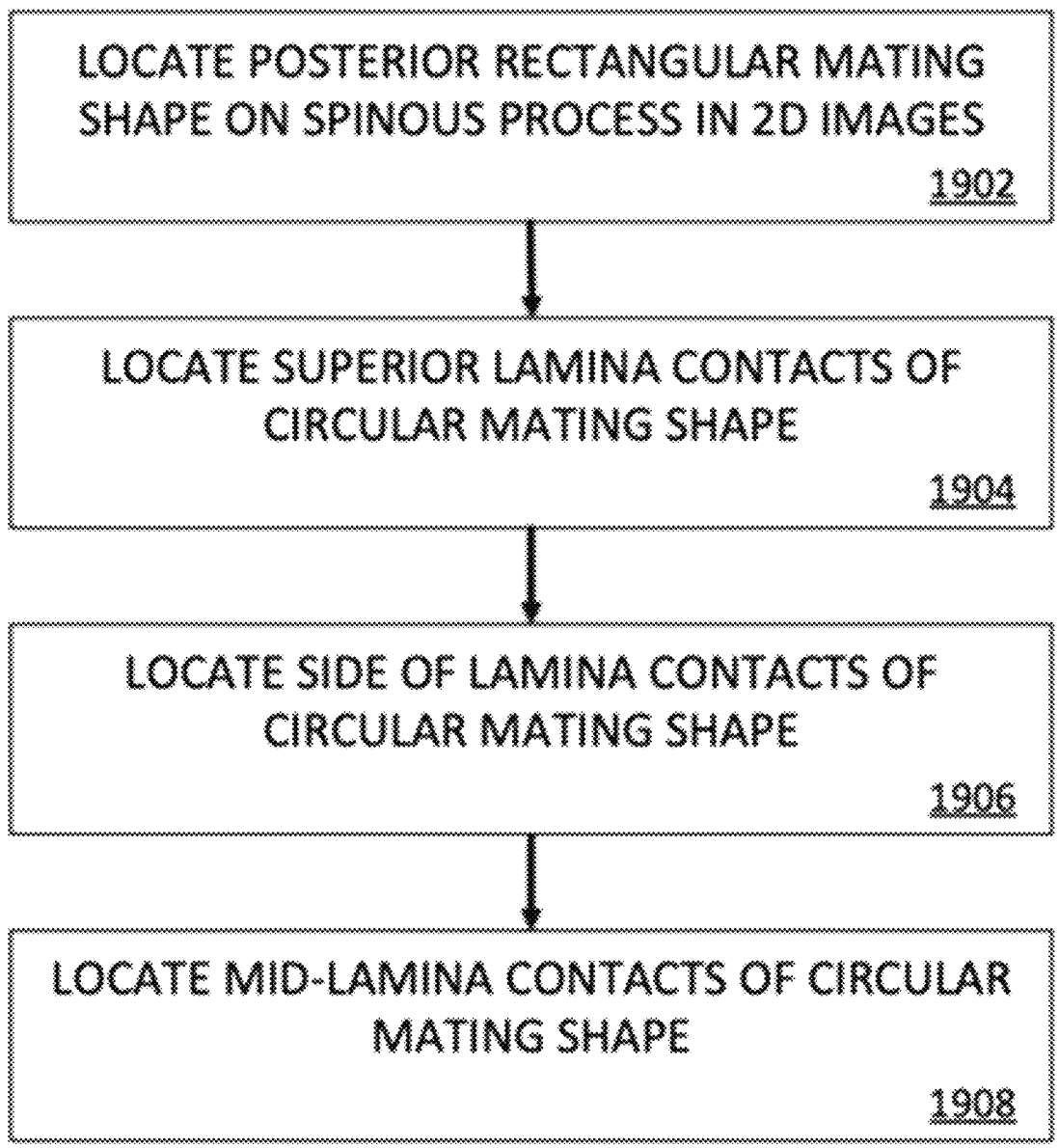
FIG. 19 is a flowchart illustrating a method for determining the contact shapes and points from a plurality of 2D images of the patient's vertebra for use in in accordance with one embodiment.

Similar to the operations described above, the operations of the method illustrated in FIG. 19 involve the operator or computing device analyzing the 2D images and utilizing, selecting one or more of the 2D images and utilizing the input device to the computing device to define a shape in the images. In particular, the computing device provides a shape on the selected image that corresponds to the surface shape of a customized MIS spine guide. The operator or computing device utilizes an input device to the computing device to locate the provided shape on the 2D image.

Beginning in operation 1902, the operator or computing device may locate a posterior rectangular mating shape on the spinous process in one of the 2D images. As explained in more detail below, this shape corresponds to a rectangular mating surface of a MIS customized spine jig that contacts the posterior portion of the spinous process. Thus, the placement of the rectangular shape in the 2D images may be translated to a machine program that creates the same or a similar shape in a customized spine guide for use in a spine procedure. In one embodiment, an operator or the computing device tabs through the various coronal 2D images of the patient's vertebra to select an image for placement of the posterior spinous process rectangular shape. In one particular example, the selected image is a coronal image slice lying between the posterior spinous process and lamina. Once the image is selected, the computing device provides a rectangular shape on the 2D image that is adjustable by the operator. An example of the rectangular shape 2004 provided in the coronal 2D image is shown in the screenshot 2002 of FIGS. 20A-20B.

Figure 20A:
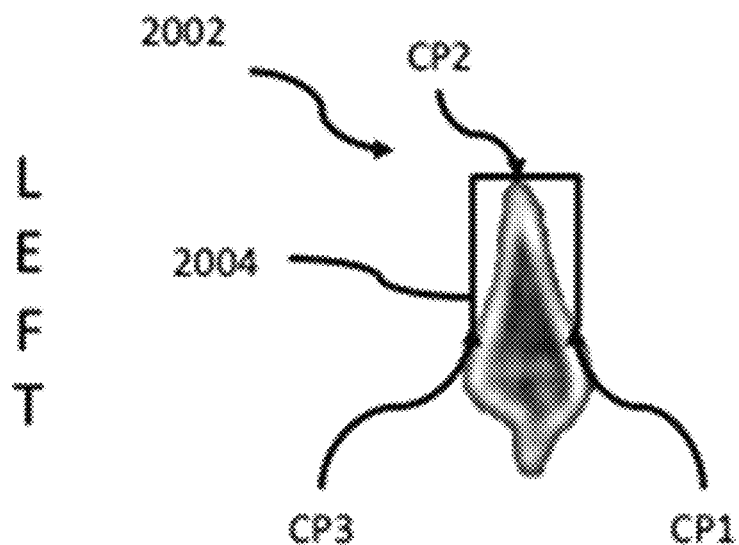
FIGS. 20A and 20 B are screenshots of a display of a spinous process in 2D coronal view indicating suitable locations of the rectangular contact points according to an embodiment.
Figure 20B:
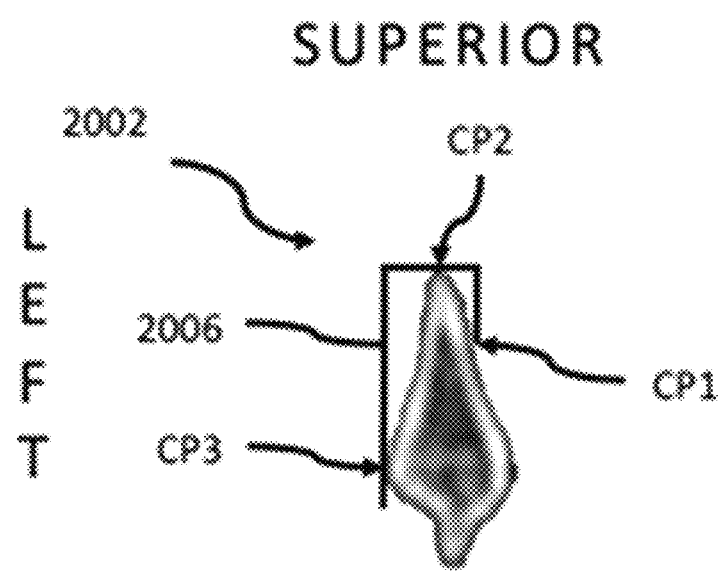

As discussed above, the computing device or user may tab through the various coronal 2D images of the patient's vertebra to select an image for placement of the posterior spinous process rectangular shape. Once the image is selected, the computing device provides a rectangular shape on the 2D image that is adjustable. An example of the rectangle shape 2004 provided in the coronal 2D image is shown in the screenshot 2002 of FIG. 20A. The operator or computing device may then move and adjust the dimensions (length and width individually) of the rectangular shape 2004 within the 2D images. In particular, the rectangular shape 2004 placed in the 2D image such that the rectangle contacts the spinous process anatomical surface at CP1, CP2 and CP3 shown in the 2D coronal image. As shown in FIG. 20A, the rectangular shape 2004 thus creates three contact points CP1, CP2, and CP3, where CP1 contacts the right side of the spinous process anatomical surface, CP2 contacts the superior side of the spinous process anatomical surface, and CP3 contacts the left side of the spinous process anatomical surface. In one embodiment, the rectangle is a hook shape 2006 in FIG. 20B also creates three contact points CP1, CP2, and CP3 on the posterior spinous process anatomical surface. The rectangular shape 2004 or 2006 is used as contact features due to its simplicity in the manufacturing process for CNC machining versus 3D printing. In general, any geometric or surface shapes that contact the three sides of the spinous process can be used. The computing device may then utilize the placement information of the rectangular shape in the 2D image and may translate that placement into the posterior spinous process rectangular shape feature of the customized jig described below.

Figure 21:
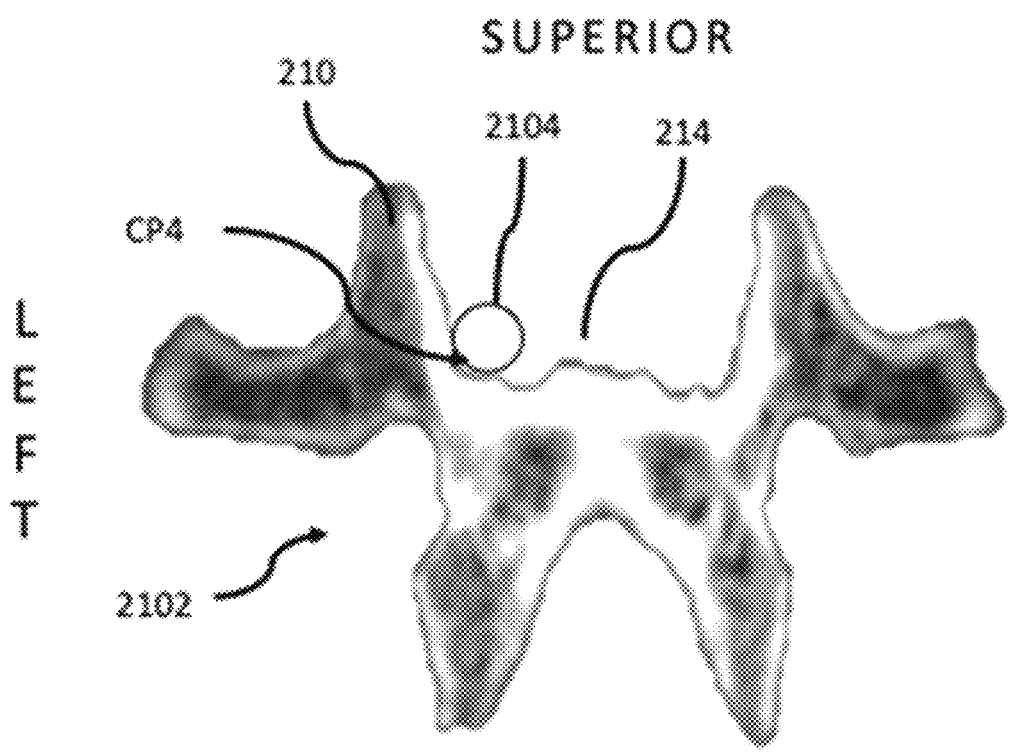
FIGS. 21 and 22 are 2D coronal screenshots of a display of upper vertebral body indicating suitable locations of the circle contact points according to an embodiment.

In operation 1904, the operator or computing device may locate superior lamina contacts of a circular mating shape in one of the 2D images. As explained in more detail below, this shape corresponds to a circular contact of a customized spine jig that contact the patient's vertebra on the superior lamina anatomical surface. Thus, the location of the superior lamina contacts of a circular mating shape in the 2D images may be translated to a machine program that creates a mating surface on a customized jig for use in a spine procedure that corresponds to the placement of the superior lamina contacts. In this manner, the superior lamina contacts of a circular mating shape is customized to the patient's vertebra as captured in the 2D images. An example of the circular shape 2104 provided in the coronal 2D image is shown in the screenshot 2102 of FIG. 21. The operator or computing device may then move and/or adjust the diameter of the circular shape 2104 within the 2D images. In particular, the circular shape 2104 is placed in the 2D image such that the circular contacts the left side of the vertebra at CP4, between the left superior facet 210 and vertebral canal 214 shown in the 2D coronal image. As shown in FIG. 21, the circular shape 2104 thus creates a contact point with the superior lamina of the patient's vertebra. The computing device may then utilize the placement information of the circular shape in the 2D image and may translate that placement into the superior lamina circular shape feature of the customized jig described below.

Figure 22:
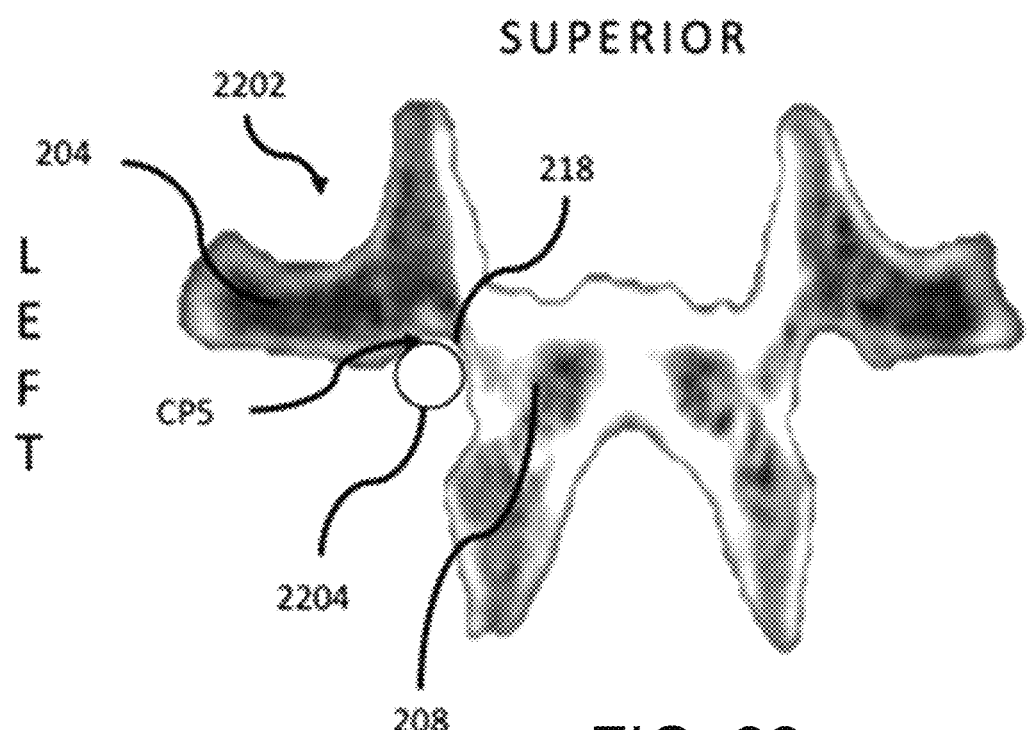

In operation 1906, the operator or computing device may locate the side lamina contacts of a circular mating shape in one of the 2D images. As explained in more detail below, this shape corresponds to a circular contact of a customized spine jig that contact the patient's vertebra on the side lamina anatomical surface. Thus, the location of the side lamina contacts of a circular mating shape in the 2D images may be translated to a machine program that creates a mating surface on a customized jig for use in a spine procedure that corresponds to the placement of the side lamina contact. In this manner, the side lamina contact of a circular mating shape is customized to either side of the patient's lamina as captured in the 2D images. An example of the circular shape 2204 provided in the coronal 2D image is shown in the screenshot 2202 of FIG. 22. The operator or computing device may move and/or adjust the diameter of the circular shape 2204 within the 2D images. In particular, the circular shape 2204 is placed in the 2D image such that the circular contacts the left side of the lamina at CP5 near the inferior vertebral notch 218, between the left transverse process 204 and lamina 208 shown in the 2D coronal image as shown in FIG. 22. The circular shape 2204 thus creates a contact point with the side lamina of the patient's vertebra. The computing device may then utilize the placement information of the circular shape in the 2D image and may translate that placement into the side lamina circular shape feature of the customized jig described below.

Figure 23:
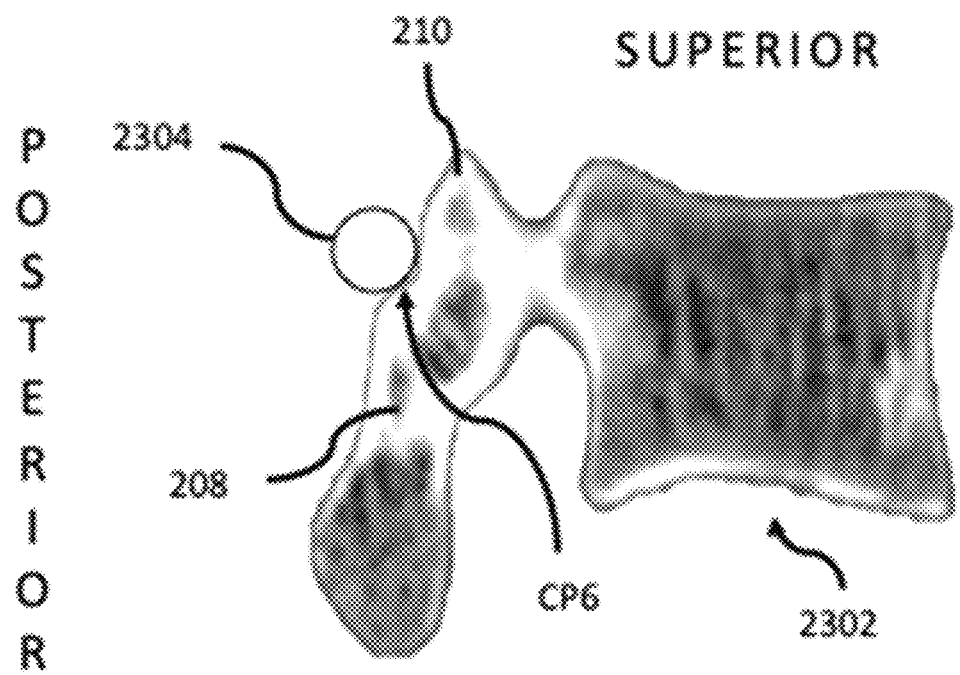
FIGS. 23 and 24 are 2D sagittal screenshots of a display of patient's lamina indicating suitable locations of the circle contact points according to an embodiment.
Figure 24:
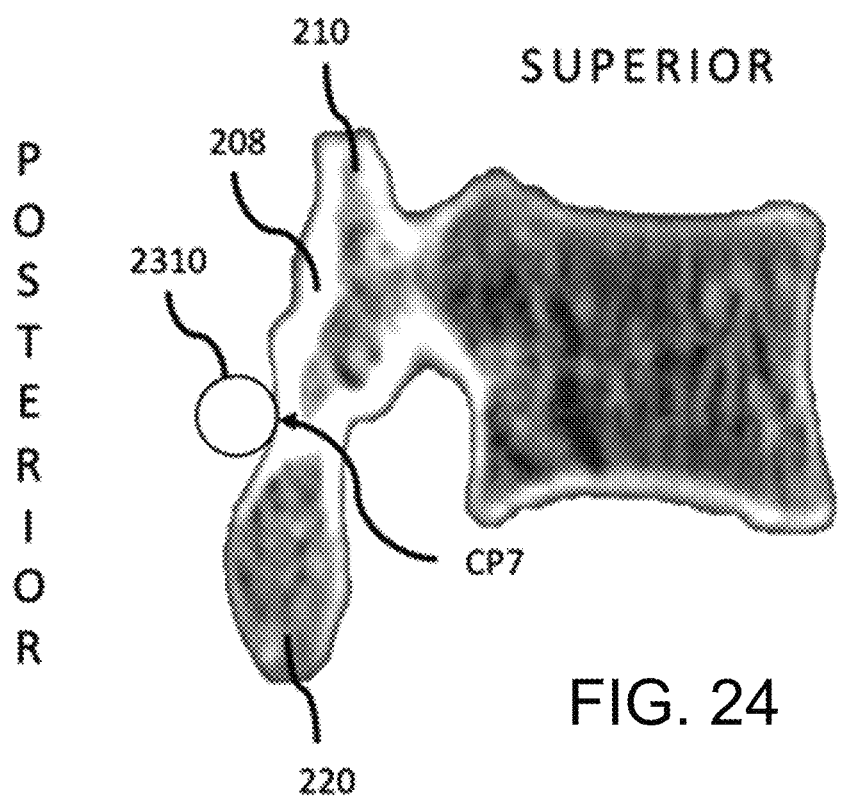

In operation 1908, the operator or computing device may locate the mid-lamina contacts of two circular mating shapes in one or more of the 2D images. As explained in more detail below, this circular shape corresponds to a mid-lamina circular contact of a customized spine jig that corresponds to the patient's vertebra on the mid-lamina anatomical surface. Thus, the location of the mid-lamina contacts of a circular mating shape in the 2D images may be translated to a machine program that creates a mating surface on a customized jig for use in a spine procedure that corresponds to the placement of the mid-lamina contact. In this manner, the mid-lamina contact of a circular mating shape is customized to the patient's vertebra captured in the 2D images. An example of the circular shape 2304 provided in the sagittal 2D image is shown in the screenshot 2302 of FIG. 23. The operator or computing device may move and/or adjust the diameter of the circular shape 2304 within the 2D images. In particular, the circular shape 2304 is placed in the 2D image such that the circular contacts the left side of the vertebra at CP6 near the superior facet 210 on the anatomical surface of lamina 208 shown in the 2D sagittal image as shown in FIG. 23. The operator may then repeat the process for the second circular mid-lamina contact point CP7, using the same 2D image as CP6 or selects a different 2D sagittal slice. In particular, the circular shape 2310 is placed in the 2D image such that the circular contacts the left side of the vertebra at CP7 near the inferior facet 220 on the anatomical surface of lamina 208 shown in FIG. 24. The circular shape 2304 and 2310 thus creates a two contact points, CP6 and CP7, with the mid-lamina anatomical surface 208 of the patient's vertebra on the left side. In general, the two mid-lamina circular contacts CP6 and CP7 are parallel to each other separated by a distance in the global coordinate system. The computing device may then utilize the placement information of the two circular shapes in the 2D image and may translate those placements into the mid-lamina circular shape features of the customized jig described below.

In a similar manner, the operator or computing device may repeat the operations in FIG. 19 for the right side of the patient's vertebra or any other vertebral segments captured in the imaging data from the imaging device 602. In one particular embodiment, the operator or computing device may perform the operations of FIG. 19 for the right and left side of the patient's vertebra simultaneously by placing additional circular contacts in operations 1904, 1906 and 1908 in the 2D image. The number of contact points may increase from 7 to 11 contact points with the addition of superior lamina circular contact point, side lamina circular contact point and two mid-lamina circular contact points for the right side of the patient's vertebra. The computing device may then utilize the placement information of the circular shape in the 2D image and may translate that placement into the corresponding circular and rectangular shape features of the customized jig for use in a spine procedure.

A customized MIS spine guide conforming to various aspects of the present disclosure includes a substrate from which various jig contact points projects are otherwise supported or defined. In one possible implementation, the jig is a unified structure formed from a block of base material using a computer numerical control (CNC) machine. However, it is possible for the jig to be an assembly of various components that form the final jig structure. Alternatively, the jig may be created through molding, machining, milling, forming, 3D printing, assembling, or other processes. The jig contact points are arranged and designed such that a surgeon may insert the jig onto the spinous process and press down on the lamina surface so that the jig will be properly positioned when the jig contact points are seated on respective vertebral contact points. Notably, there are a discrete number of jig contact points (e.g., CP1-CP7) as opposed to full surfaces or far more numerous numbers of contact locations. When the jig is seated on the vertebra, the surgeon may hold the jig in the proper position on the vertebra so that drilling of the pedicle may be performed pursuant to a spinal procedure.

In the view illustrated in FIG. 25A, a portion of a coronal plane MRI, CT or X-ray slice of the posterior spinous process is illustrated. More specifically, the continuous curve represents a coronal plane MR, CT or X-ray slice of the spinous process encompassing three jig contact points JP1-JP3. In order to define the jig contact points JP1-JP3, various lines, curve (y=f(x)) and geometrical shapes may be deployed. In the case of FIG. 25A, a rectangle is used to define the three jig contact points JP1-JP3 at the corresponding posterior spinous contact points. In general, a rectangle is used to define three (3) contact points on the same plane in the 2D images.

In the case of FIG. 25B, a circle is used to define the jig contact points at the corresponding lamina contact points on the vertebra anatomical surface. The continuous curve represents a MRI, CT or X-ray slice of lamina, for example, encompassing at least one or more contact points on the lamina anatomical surface. In order to define the jig contact points JP4-JP7, various lines, curves (y=f(x)) and geometrical shapes may be deployed. In the case of FIG. 25B, a circle is used to define a jig contact point, such as JP4, JP5, JP6 or JP7, at the corresponding lamina contact points CP4-CP7. In general, a circle is used to define one or more anatomical contact points on the same plane in the 2D images.

Figure 26:
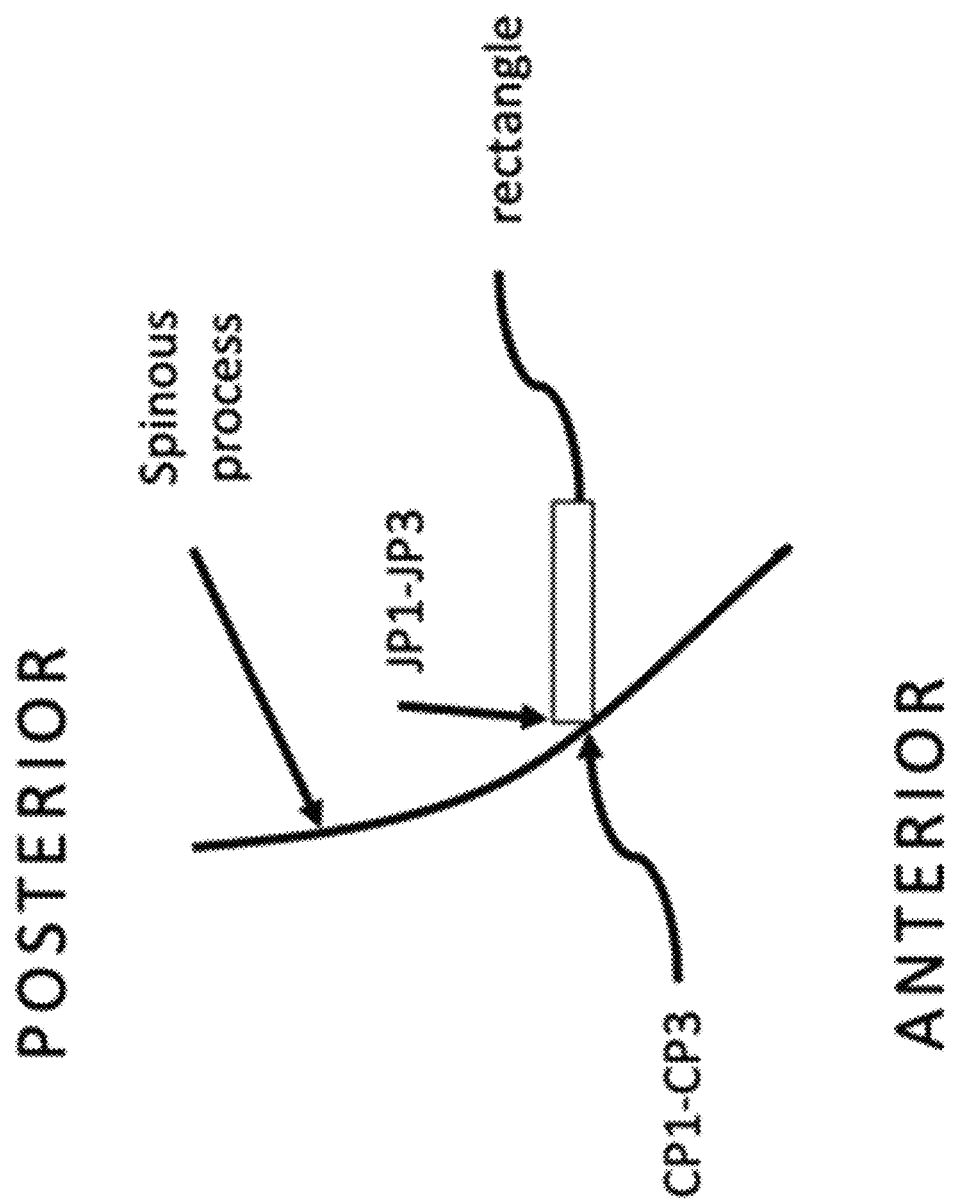
FIG. 26 is an isometric view of patient's spinous process portion indicating suitable contact point according to an embodiment.
Figure 27:
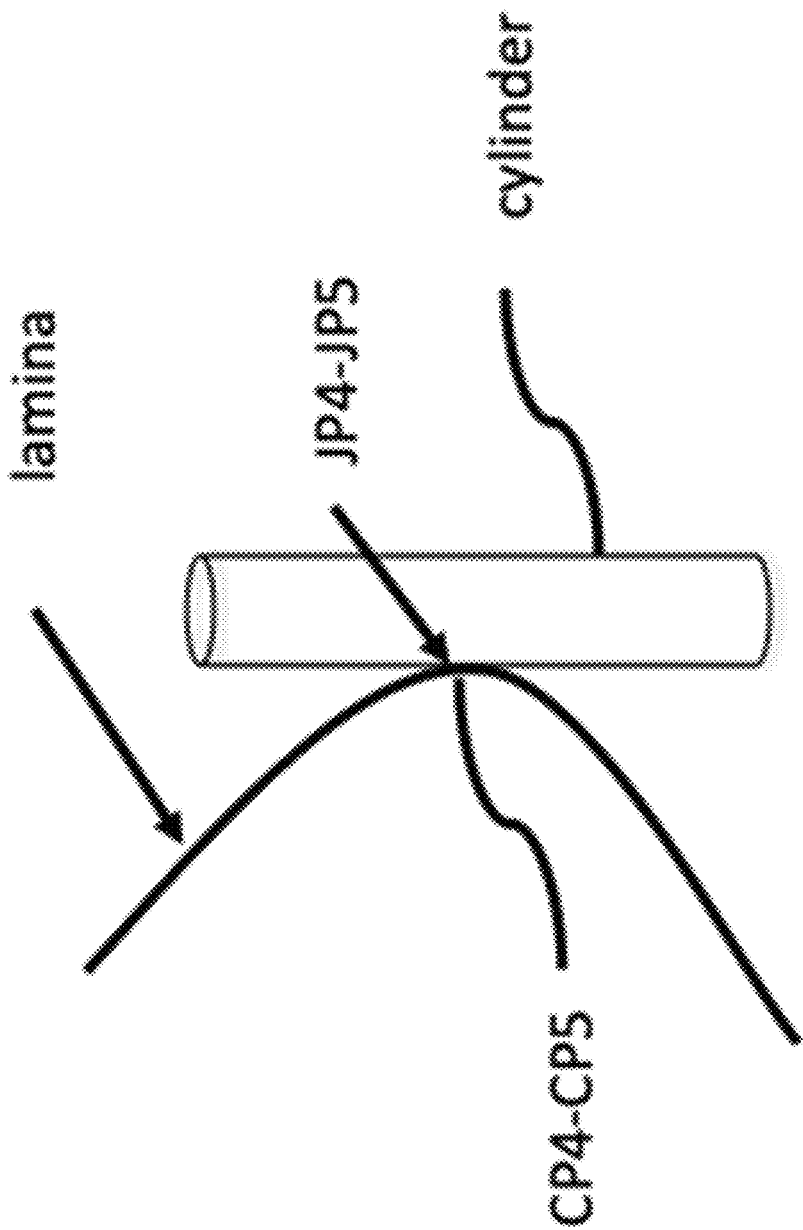
FIG. 27 is an isometric view patient's lamina portion indicating suitable contact point according to an embodiment.
Figure 28:
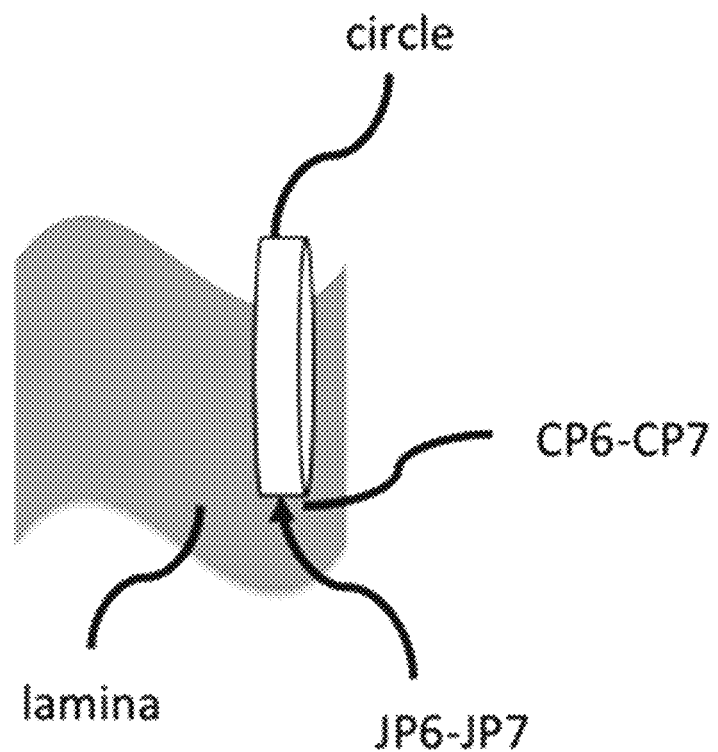
FIG. 28 is an isometric view patient's vertebral body portion indicating suitable contact point according to an embodiment.
Figure 29A:
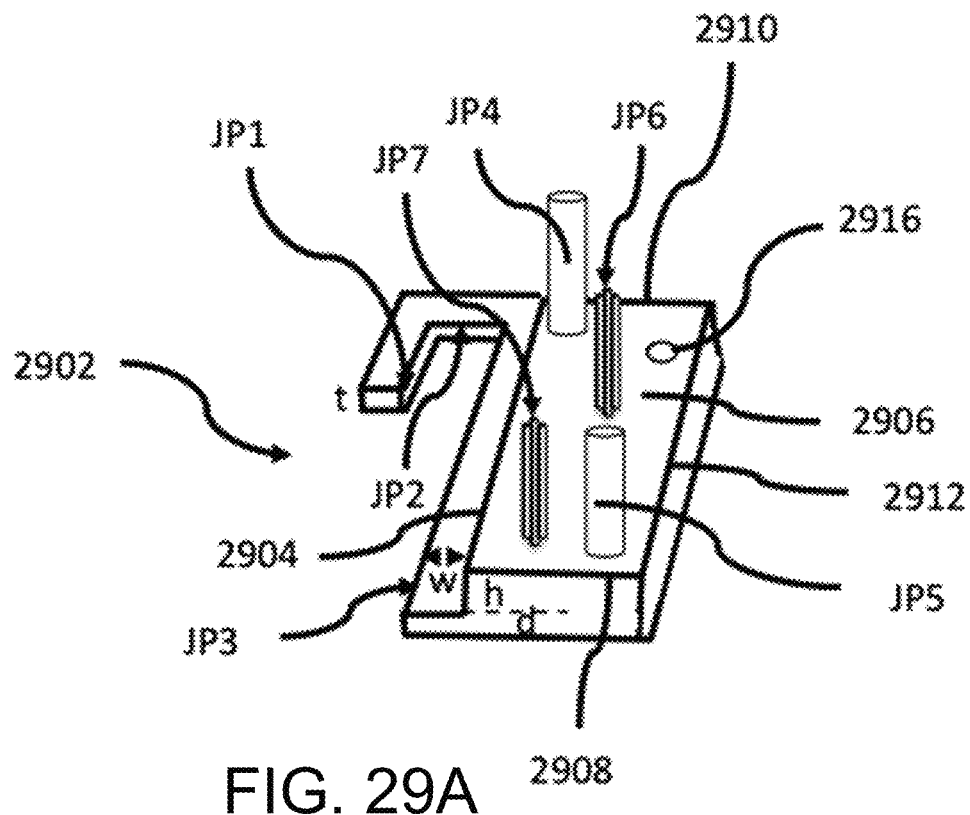
FIGS. 29A and 29B are isometric views of the embodiment indicating the jig mating shapes corresponding to the contact points identified in 2D images.
Figure 29B:
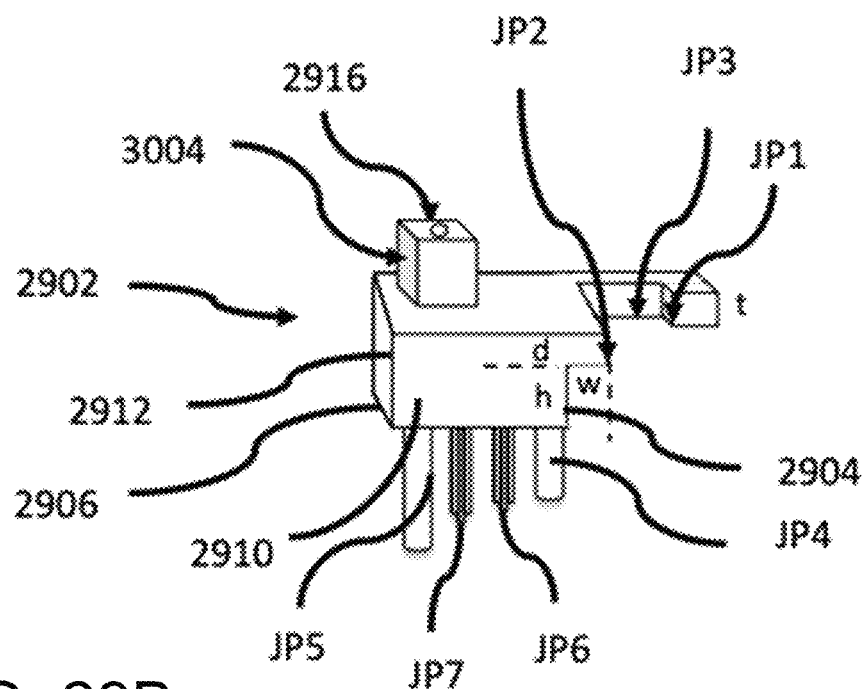
Figure 30:
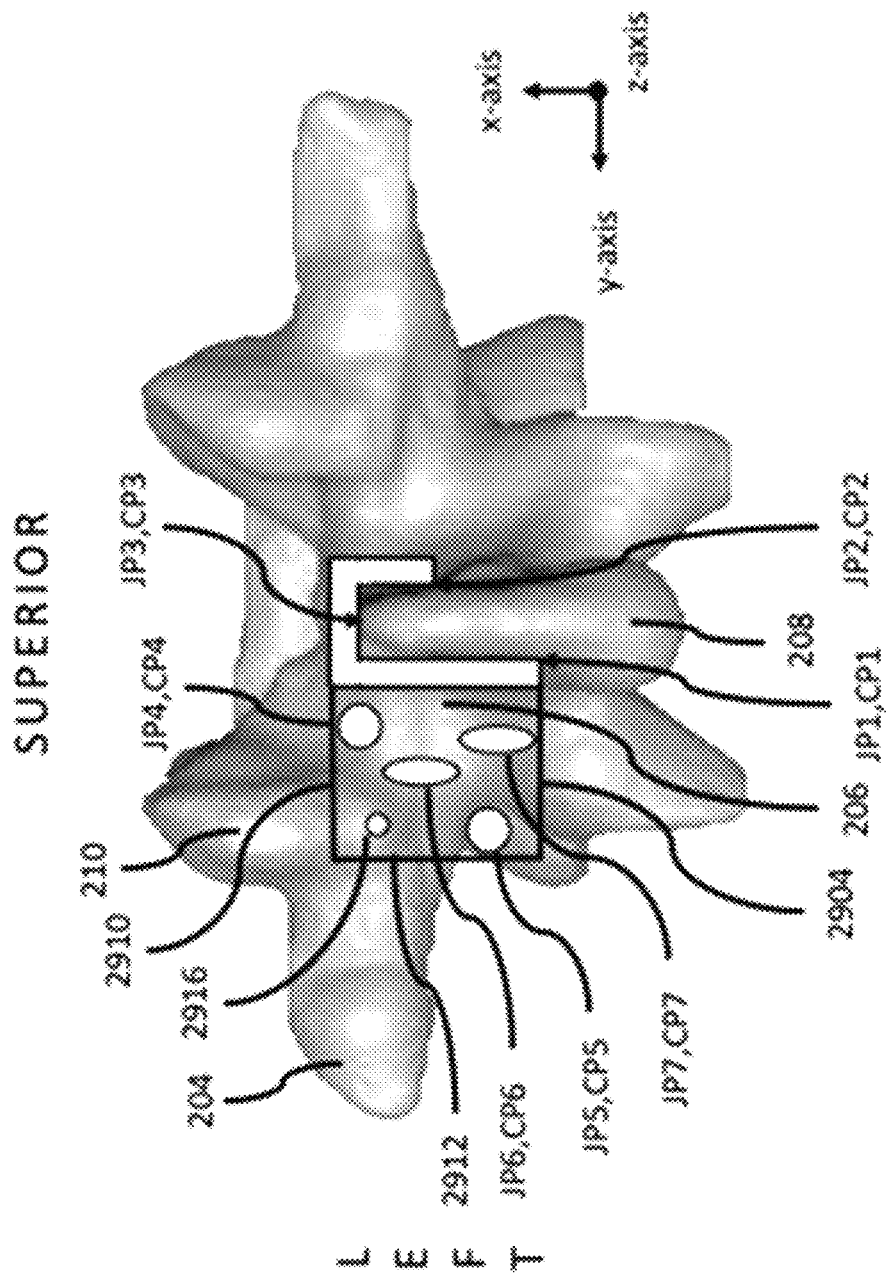
FIGS. 30-32 are isometric views of the patient's lumbar vertebra illustrating the embodiment jig features and contact points according to an embodiment.

FIGS. 26-28 are schematic views of the isometric views of the jig 2902 in FIGS. 29-30 showing suitable positions for the seven (7) jig contact points JP1-JP7. FIG. 26 is a representative axial plane view of the spinous process (a portion of the spinous process illustrated may be cortical bone, cancellous bone or cartilage) containing CP1-CP3 and illustrating a jig feature (a portion rectangle) defining the jig contact points JP1-JP3 contacting the posterior spinous process at CP1-CP3. The posterior spinous process contact points CP1, CP2 and CP3 are in the same coronal plane with corresponding jig contact points JP1, JP2 and JP3. However, such a co-planar arrangement is not necessary. For example, it would be possible for CP1, CP2 and CP3 to be on 3 different coronal planes spaced apart by any distance or any combination of CP1, CP2 and CP3 to be on the same plane. Alternatively, the contact points may be defined on other surfaces or 2D projections.

FIG. 27 is a representative axial plane view of the lamina (a portion may be cortical bone, cancellous bone or cartilage) containing CP4-CP5 and illustrating a jig feature (a portion cylinder) defining the jig contact points JP4-JP5 contacting the superior and side of lamina at CP4-CP5. The superior and side of lamina points CP4-CP5 can be in the same coronal plane with corresponding jig contact points. However, such a co-planar arrangement is not necessary. For example, it would be possible for CP4-CP5 to be on different coronal planes spaced apart any distance. Alternatively, the contact points may be defined on other surfaces or 2D projections.

FIG. 28 is a representative axial plane view of the lamina (a portion may be cortical bone, cancellous bone or cartilage containing) CP6-CP7 and illustrating a jig feature (a portion circle) defining the jig contact points JP6-JP7 contacting the mid-lamina at CP6-CP7. The mid-lamina points CP6-CP7 can be in the same sagittal plane with correspond jig contact points JP6-JP7. However, such a co-planar arrangement is not necessary. For example, it would be possible for CP6-CP7 to be on different sagittal planes spaced apart at any distance. Alternatively, the contact points may be defined on other surfaces or 2D projections.

Referring now to FIGS. 29A-29B, the jig includes a main substrate portion 2906 with certain dimensions (width (2904-2912) by length (2910-2908) by height (h+d) in mm) and various geometric features, such as rectangular and curvilinear shapes, projecting from the surface of the main substrate 2906. In general the main substrate 2906 is parallel to the coronal plane or perpendicular to the z-axis when mounted on the patient's vertebra. As discussed above, the main substrate 2906 may also be perpendicular to the center-axis 1604 of the pedicle. With a CNC machine created jig, the rectangular shape and flat surface is an efficient and effective way to define the main substrate 2906. However with a 3D printed jig, the main substrate can be more conforming to the patient's anatomy and need not to be defined by a rectangular dimension such as the jig 2902 shown in FIGS. 29A-29B.

As discussed above, the jig implantation illustrated includes seven (7) contact points. However, it is possible to provide a jig with slightly more or slightly fewer contact points. Starting with the rectangular jig feature as shown in FIG. 26 with contact point JP1-JP3 with thickness t, approximately 2 mm, but will typically fall within the range of 15 mm to 20 mm depending on the patient's anatomy. The jig rectangular feature at JP3 may be separated by a distance (w) from the main substrate portion 2904, approximately 2 mm, but will typically fall between 0 mm to 10 mm depending on the patient's anatomy. Also, the relative position of the rectangular contact features JP1-JP3 need not be co-planar or bounded by the main substrate 2906 as discussed above. However as can be seen in FIGS. 29A-29B, the rectangular features JP1-JP3 is generally bounded by substrate portion 2910 and 2908 and projecting from substrate portion 2904. It should be noted that the rectangular jig features depend on the locations of corresponding contact points CP1-CP3 in the 2D images. Hence the jig rectangular positions, projections and dimensions on the vertebra will vary based on the anatomy of the patient, the type of procedure, the type of implant or instruments, and any number of other factors.

As discussed above, the first 3 contact points are associated with the jig rectangular feature. The remainder 4 contact points are associated with the jig curvilinear features for contact points JP4-JP7. The jig curvilinear features with contact points JP4-JP5 are cylinders as shown in FIG. 27 with adjustable diameters set by the operator or computing device and approximately 10 mm in length, but will typically fall within the range of 20 mm to 24 mm depending on the patient's anatomy. In addition, the jig curvilinear features with contact points JP6-JP7 are partial circles as shown in FIG. 27 with adjustable diameters set by the operator or computing device and approximately 10 mm in length, but will typically fall within the range of 20 mm to 24 mm depending on the patient's anatomy. As discussed above, the relative position of the curvilinear contact features JP4-JP7 need not be co-planar or bounded by the main substrate 2906. However as can be seen in FIGS. 29A-29B, the curvilinear features JP4-JP7 are generally bounded by substrate portion 2910, 2908, 2904 and 2912 projecting from substrate portion 2906 and perpendicular to the jig rectangular feature projected from portion substrate 2904. It should be noted that the curvilinear jig features depend on the locations of corresponding contact points CP4-CP7 in the 2D images. Hence the jig curvilinear positions, projections and dimensions on the vertebra will vary based on the anatomy of the patient, the type of procedure, the type of implant or instruments, and any number of other factors.

As shown in FIGS. 29A-29B, the aperture 2916 extends through the respective rectangular boss 3004 feature and the substrate surface 2906. The rectangular boss feature can be used as a trajectory guide for various instruments and implants as discussed above. The shape of the boss 3004 can be any geometric shape, such as square or cylindrical, depending on the instrument and implant used during the surgical procedure. Generally the aperture angle in the global coordinate system is the same as the pedicle screw axis 1604 of the vertebra. It should be noted that the aperture 2916 of the boss feature 3004 represents the trajectory axis 1604 of the various implants (e.g. pedicle screw) and instruments (e.g. drill bits, k-wires, taps) while the boss 3004 feature guides the various implant and instrument with different surface shapes and diameters, and hence the boss portion of the jig will vary based on the anatomy of the patient, the type of procedure, the type of implant or instruments, and any number of other factors. Hence, the anatomical relationships described are illustrative and not limiting.

The various features discussed and shown herein are but one way to create a jig defining the various jig contact points of interest. In the example shown, the CNC machine tool bits and other cutting mechanisms influence the jig shapes. The various surfaces and jig features, on which the jig contact points are defined, are thus defined in part by requirements of the CNC machine. If the jig were formed in another way, such as through 3D printing or molding, the jig contact point features and overall jig shape may be different than illustrated although the position and relative location of the jig contact points, depending on the patient, would be substantially the same regardless of the jig manufacturing technique employed.

Figure 31:
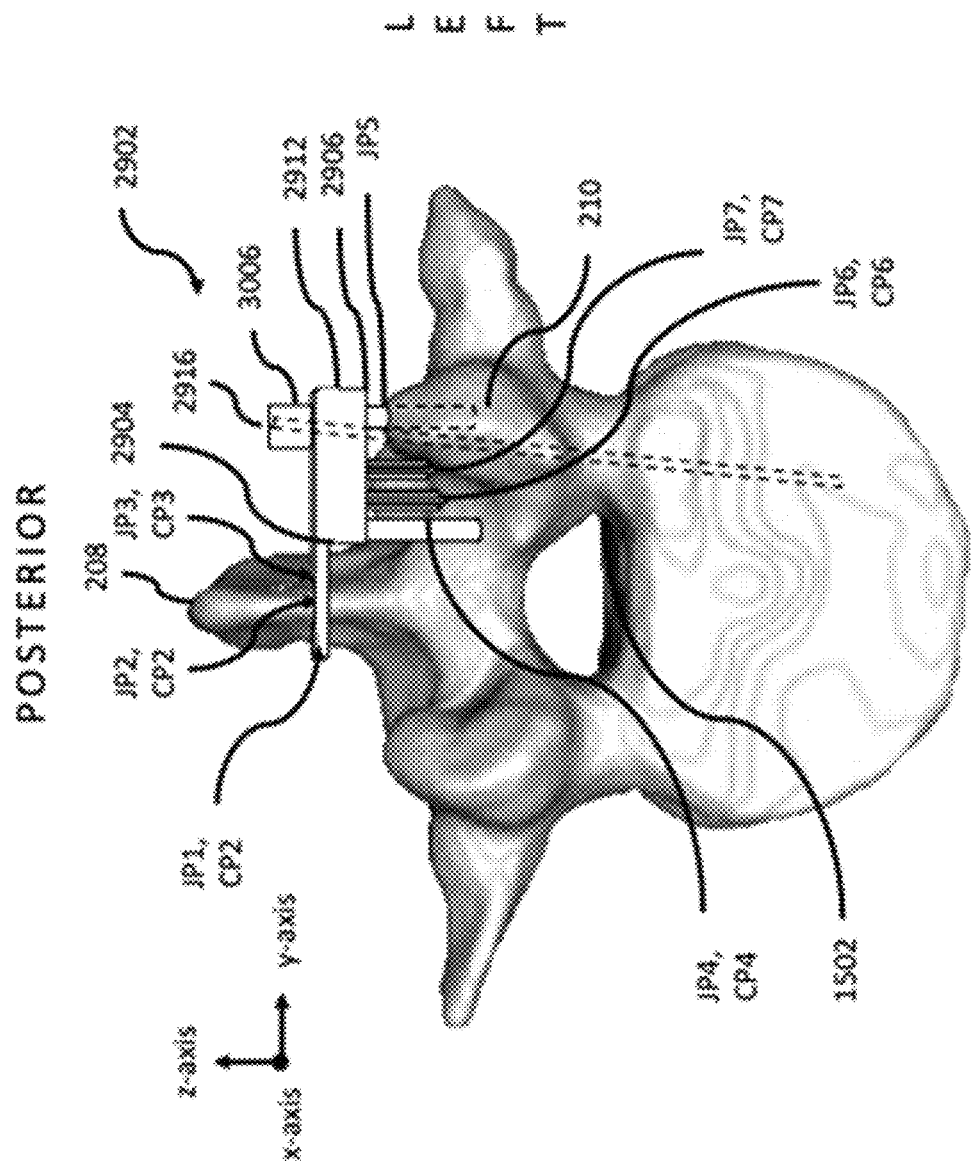
Figure 32:
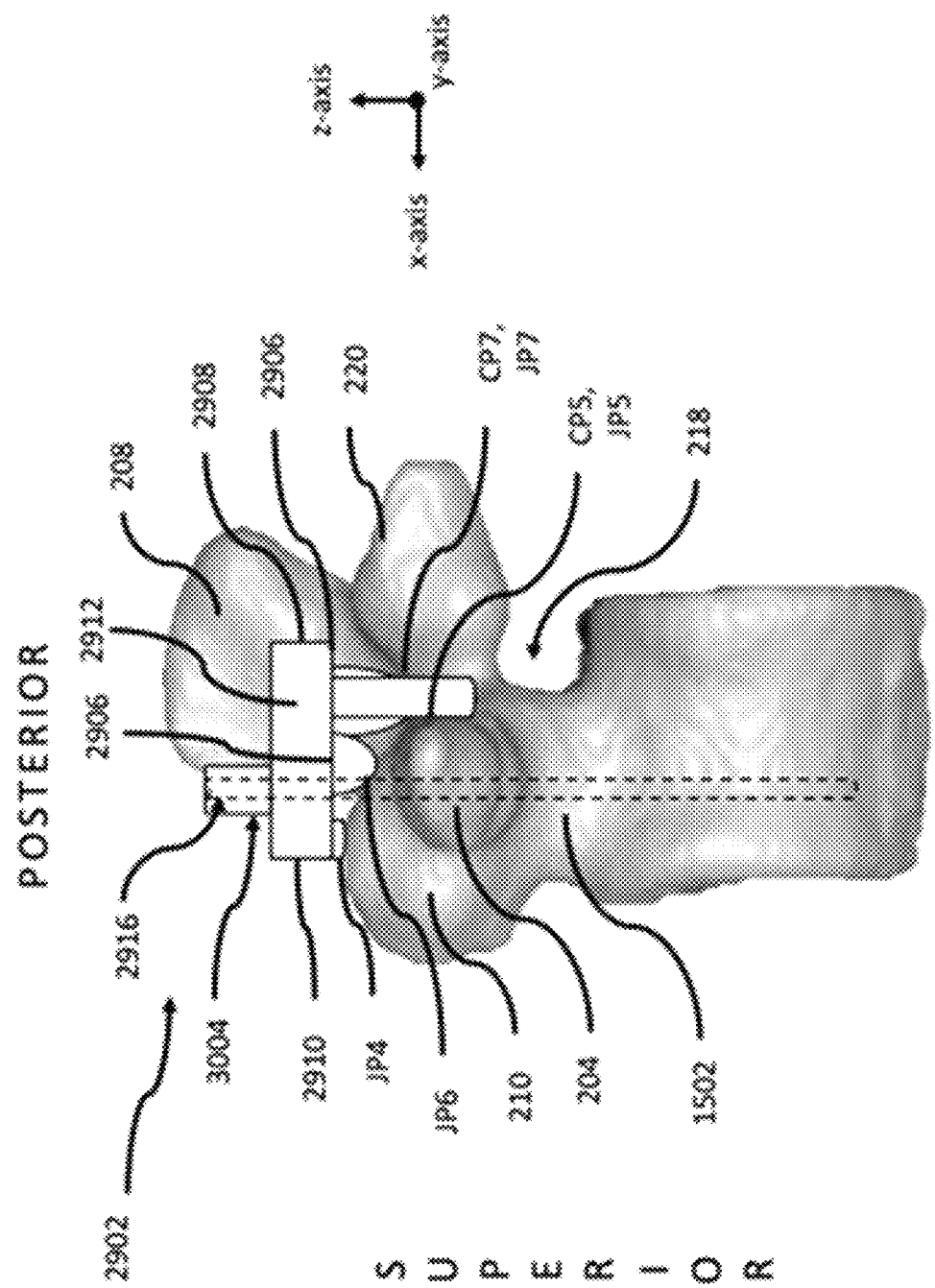

Referring now to FIGS. 30-32, which are isometric views of the jig 2902 mounted on the patient's vertebra for establishing the implant and instrument trajectory for the left pedicle. As shown in FIG. 30, the jig rectangular feature with contact points JP1-JP3 is inserted onto the spinous process 208 from the superior end. When jig contact point JP3 mates with superior spinous process contact point CP3, this prevents the guide from extending further along the x-axis while JP1-JP2 aligns the jig in the proper orientation around the z-axis of the global coordinate system using contact points CP1-CP3 as surface references. Connected to the jig rectangular feature is the main substrate with boundaries 2910, 2912 and 2904. These main substrate 2906 boundaries encompass the jig curvilinear features contact points JP4-JP7 with corresponding contact points CP4-CP7. The boundary line 2910 is generally between the superior facet 210 and posterior spinous process 208 along the mid-transverse process 204 depending on the location on position of contact points CP3 and CP4. The boundary line 2912 is generally along the mid superior facet joint 210 extending beyond the side lamina contact point CP5 and aperture 2916. The boundary line 2904 is generally near the inferior facet joint including the mid-lamina 208 extending beyond the mid-lamina contact point CP7 and CP1. In general, the main substrate boundaries 2910, 2912 and 2904 can be any lengths and shapes to encompass the jig curvilinear features JP4-JP7 and connects with the jig rectangular feature JP1-JP3. In addition to the jig rectangular feature JP1-JP3, the curvilinear feature JP4-JP5 when mounted on the patient's vertebra prevents the guide from rotating about the z-axis as well as translating along the y-axis. In general, the position and orientation of the jig would give the operating surgeon a visual queue to reposition the jig if unstable or incorrect.

FIG. 31 is an axial view of the jig 2902 mounted on the patient's vertebra for establishing the implant and instrument trajectory for the left pedicle. The jig rectangular feature with contact points JP1-JP3 is mounted onto the posterior spinous process 208 from the superior end. When jig contact point JP3 mates with superior spinous process contact point CP3, jig contact points JP1 and JP3 prevents the guide from moving further along the y-axis of the global coordinate system. Also shown in FIG. 30, the distance (w) in FIG. 29A is determined from JP3 and boundary line 2904 to avoid any interference with base of the spinous process 208. The jig curvilinear features JP4-JP7 project anteriorly from main substrate 2906. Jig contact point JP4 is between the superior facet 210 and spinous process 208 making contact with the superior lamina at contact point CP4. In general, the cylindrical feature JP4 may not interfere with the inferior facet of the previous vertebra or violate or interfere with vertebral canal. In between JP4 and JP5 are the partial circle (curvilinear shape) jig features JP6 and JP7 extending from the main substrate 2906 and making contact with the mid-lamina surface at contact points CP6 and CP7. In general, the partial circle jig contact point JP6 and JP7 presents the guide from translating along the z-axis when the jig is pressed onto the patient's vertebra. In addition the jig contact points JP6 and JP7 along with JP1 and JP2, acts like a lever arm preventing the jig from rotating about the x-axis of the global coordinate system. The length of the partial circles JP6-JP7 extending from main substrate 2906 along with the thickness of the substrate (h+d) are not touching the superior facet joint to interfere with the mounting of the guide on the patient's vertebra. The boundary line 2912 of main substrate 2906 may extend beyond jig contact point JP5 including the aperture 2916 and boss 3006 feature so that the pedicle 1502 trajectory extends through the substrate 2906 surface.

FIG. 32 is sagittal view of the jig 2902 mounted on the patient's vertebra for establishing the implant and instrument trajectory for the left pedicle. The jig curvilinear features JP4-JP7 project anteriorly from main substrate 2906. Jig contact point JP5 is near the inferior vertebral notch and transverse process 204 making contact with the inferior transverse process beyond the widest part of the bone at contact point CP5. In general, the cylindrical feature, JP5, will not interfere with the inferior vertebral notch or violate or interfere with vertebral nerve. In addition, the JP4-JP5 along with rectangular jig contact point JP2 prevents the guide from rotating about the y-axis and translating along the x-axis. In between JP4 and JP5 are the partial circle jig features (curvilinear shape) JP6 and JP7 extending from the main substrate 2906 and making contact with the mid-lamina surface at contact points CP6 and CP7. In general, the partial circle jig contact point JP6 and JP7 prevents the guide from translating along the z-axis when the jig is pressed onto the patient's vertebra. The length of the partial circles JP6-JP7 (curvilinear shape) extending from main substrate 2906 along with the thickness of the substrate (h+d) are not be touching the superior facet joint to interfere with the mounting of the guide on the patient's vertebra. The boundary line 2910 of main substrate 2906 may extend beyond jig contact point JP4 including the aperture 2916 and boss 3006 feature so that the pedicle 1502 trajectory extends through the substrate 2906 surface. In addition, the boundary line 2908 of main substrate 2906 may extend beyond jig contact point JP3, JP5 and JP6 between the transverse process 204 and inferior facet 220.

Figure 33A:
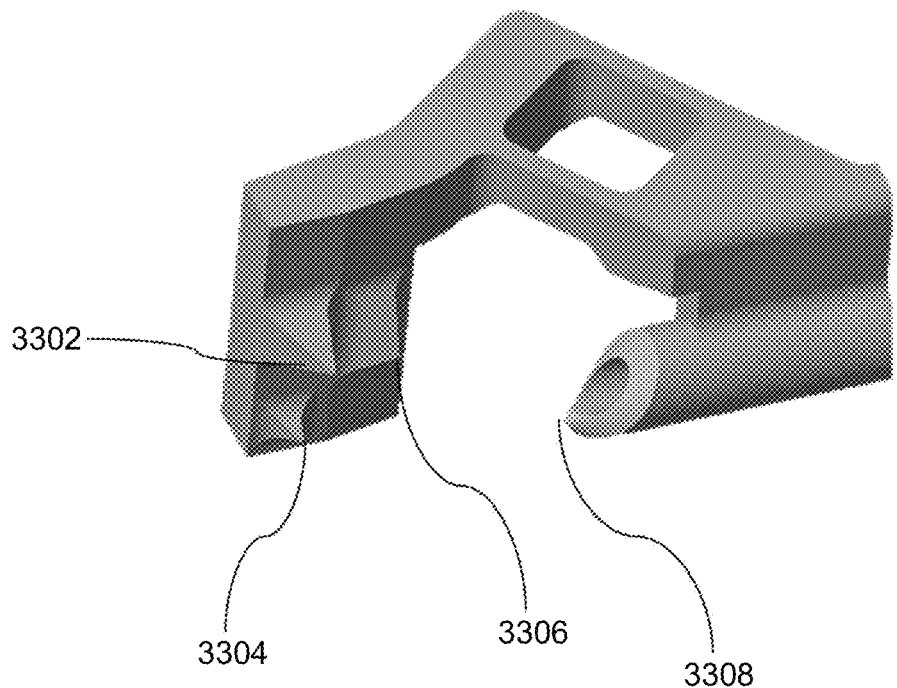
FIGS. 33A-33B are isometric views of a second embodiment of the implant jig corresponding to the contact points identified in 2D images.
Figure 33B:
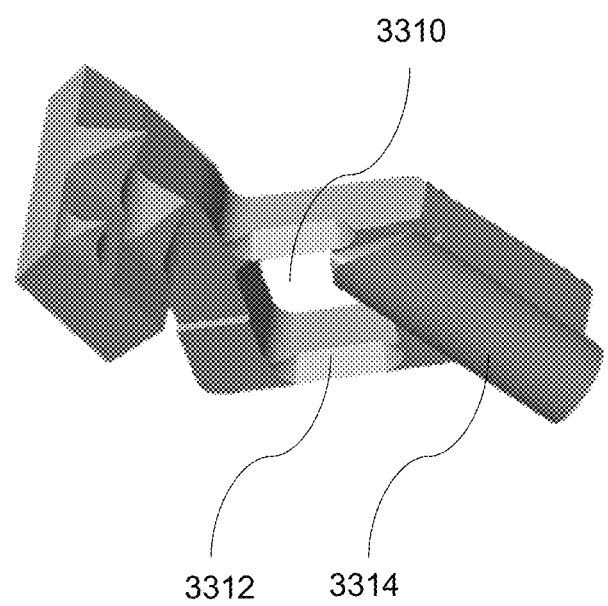

FIGS. 33A-33B are isometric views of a second embodiment of the implant jig corresponding to the contact points identified in 2D images. This embodiment of the implant jig includes three contact points 3302-3306 that mate along a lateral aspect of the pedicle of the patient's vertebrae and a conical or circular contact point 3308 that mates below the pedicle screw entry point. When mated, lines 3312 and 3314 may rest across the superior aspect of the transverse process of the patient's vertebrae. The implant jig includes a drill guide 3316 through which the pedicle screw may be inserted, as discussed above.

The implant jig of FIGS. 33A-33B may contact the patient's vertebrae with three different orientations around the transverse process for a secure fit. In particular, the implant jig may include three contact points 3302, 3304, and 3306 that touch three points along the lateral aspect of the pedicle. An additional two contact points 3310 and 3312 may contact the superior portion of the transfer process of the vertebrae and one contact point 3308 may contact the posterior portion of the pedicle near a screw center point (such as SCP in FIG. 18C). This embodiment provides at least one contact point in each of three orientations around the vertebrae to provide a secure connection to the vertebrae. To mount the implant jig on the vertebra, the jig may be tranversed along the transfer process from superior to inferior until the two contact points 3310 and 3312 makes contact with the superior transfer process. The three contact points 3302, 3304, and 3306 near the lateral aspect of the pedicle from transverse process to the vertebral body (inflection point) provide rotational support (pivot point) for the implant jig since the typical axial trajectory for lumbar is ~30 Deg from vertical and for thoracic is ~20 Deg from vertical. The posterior contact point 3308 near the screw entry point provides stability when drilling the screw or guide wire into the pedicle. Since the tip screw or drill bit may be conical in shape to easily penetrate the cortical bone, the tip tends to walk or slide on the surface of the bone when drilling at an angle without a drill guide near the bone surface. The contact point on the posterior portion of the pedicle 3308 prevents the screw or drill bit from walking, bending or sliding.

In still another embodiment, the three contact points 3302, 3304, and 3306 on the lateral aspect of the pedicle near the inflection point can be a point, line, rectangle, circle or cylinder similar to FIGS. 25B-28. The two contact points 3310 and 3312 of the superior transfer process can be a line, triangle, rectangle or slot making contact on the superior, posterior and anterior portion of the transfer process similar to FIG. 20A. The posterior contact 3308 points near the SCP can be a point (conical), cylinder or circle.

Figure 34:
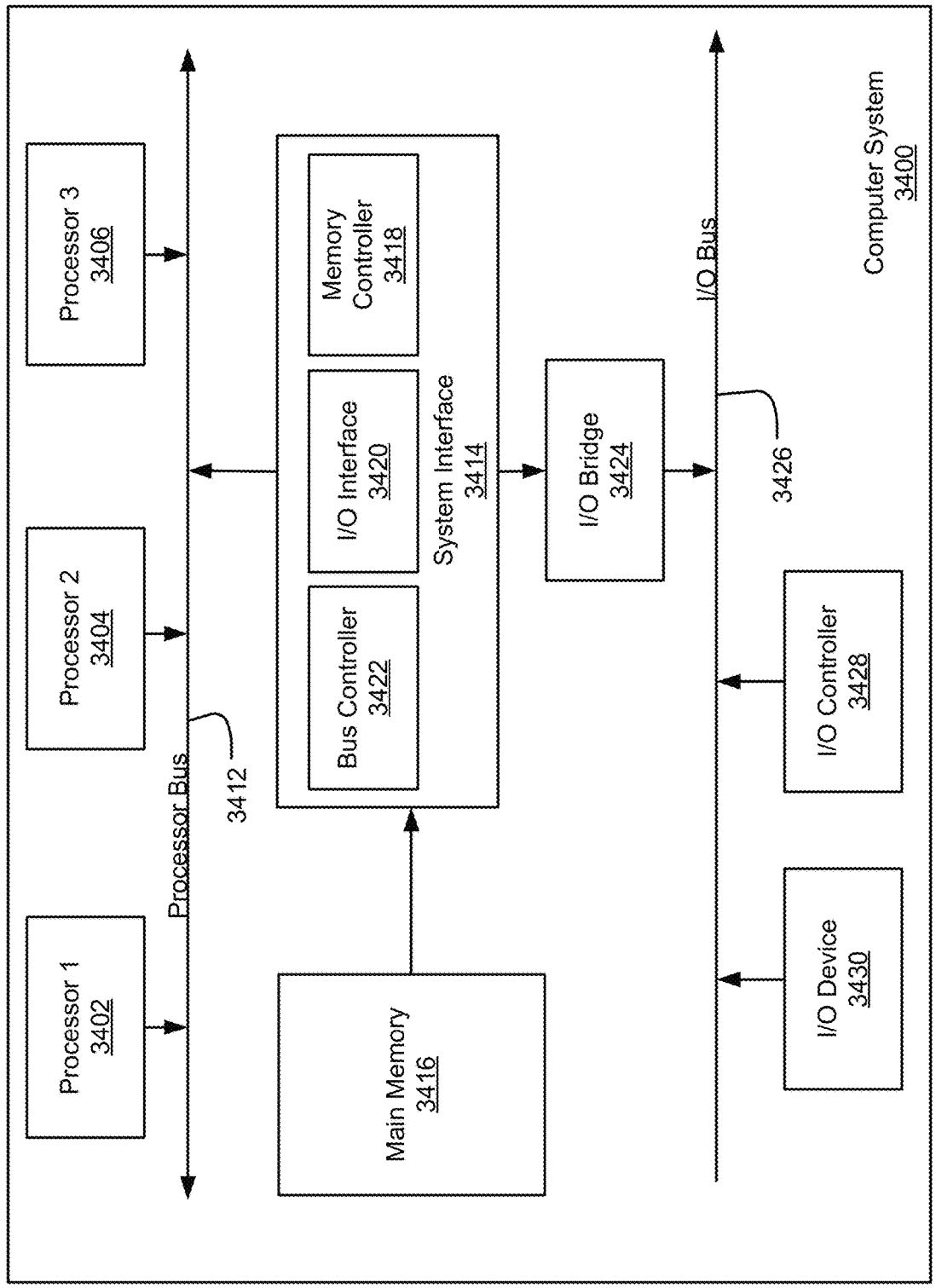
FIG. 34 is a diagram illustrating an example of a computing system which may be used in implementing embodiments of the present disclosure.

FIG. 34 is a block diagram illustrating an example of a computing device or computer system 3400 which may be used in implementing the embodiments of the components of the network disclosed above. For example, the computing system 3400 of FIG. 34 may be the traffic controller device 340 discussed above. The computer system (system) includes one or more processors 3402-3406. Processors 3402-3406 may include one or more internal levels of cache (not shown) and a bus controller or bus interface unit to direct interaction with the processor bus 3412. Processor bus 3412, also known as the host bus or the front side bus, may be used to couple the processors 3402-3406 with the system interface 3414. System interface 3414 may be connected to the processor bus 3412 to interface other components of the system 3400 with the processor bus 3412. For example, system interface 3414 may include a memory controller 3414 for interfacing a main memory 3416 with the processor bus 3412. The main memory 3416 typically includes one or more memory cards and a control circuit (not shown). System interface 3414 may also include an input/output (I/O) interface 3420 to interface one or more I/O bridges or I/O devices with the processor bus 3412. One or more I/O controllers and/or I/O devices may be connected with the I/O bus 3426, such as I/O controller 3428 and I/O device 3430, as illustrated.

I/O device 3430 may also include an input device (not shown), such as an alphanumeric input device, including alphanumeric and other keys for communicating information and/or command selections to the processors 3402-3406. Another type of user input device includes cursor control, such as a mouse, a trackball, or cursor direction keys for communicating direction information and command selections to the processors 3402-3406 and for controlling cursor movement on the display device.

System 3400 may include a dynamic storage device, referred to as main memory 3416, or a random access memory (RAM) or other computer-readable devices coupled to the processor bus 3412 for storing information and instructions to be executed by the processors 3402-3406. Main memory 3416 also may be used for storing temporary variables or other intermediate information during execution of instructions by the processors 3402-3406. System 3400 may include a read only memory (ROM) and/or other static storage device coupled to the processor bus 3412 for storing static information and instructions for the processors 3402-3406. The system set forth in FIG. 34 is but one possible example of a computer system that may employ or be configured in accordance with aspects of the present disclosure.

According to one embodiment, the above techniques may be performed by computer system 3400 in response to processor 3404 executing one or more sequences of one or more instructions contained in main memory 3416. These instructions may be read into main memory 3416 from another machine-readable medium, such as a storage device. Execution of the sequences of instructions contained in main memory 3416 may cause processors 3402-3406 to perform the process steps described herein. In alternative embodiments, circuitry may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media and may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 3406 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in main memory 516, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

It should be noted that the flowcharts above are illustrative only. Alternative embodiments of the present invention may add operations, omit operations, or change the order of operations without affecting the spirit and scope of the present invention. The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

Embodiments of the present disclosure include various steps, which are described in this specification. The steps may be performed by hardware components or may be embodied in machine-executable instructions, which may be used to cause a general-purpose or special-purpose processor programmed with the instructions to perform the steps. Alternatively, the steps may be performed by a combination of hardware, software and/or firmware.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations together with all equivalents thereof.

I claim:

1. A method for creating an implant jig for a surgical spinal procedure, the method comprising:
   receiving, at a computing device, a plurality of two-dimensional images of a patient's vertebrae that is the subject of a spinal procedure;
   reformatting the two-dimensional images, via an identification of a plurality of portions of the patient's vertebrae within the plurality of two-dimensional images, to approximate a true anatomical coordinate of the patient's vertebrae;
   locating a plurality of mating shapes within the reformatted plurality of two-dimensional images of the patient's vertebrae by receiving an indication, within the at least one of the plurality of two-dimensional images, a position of a first circular mating shape such that the first circular mating shape contacts a superior lamina, between a superior facet and a vertebral canal, on a first side of the patient's vertebrae as illustrated in the at least one of the plurality of two-dimensional images, the first circular mating shape corresponding to a first tubular mating shape of the implant jig, the plurality of mating shapes corresponding to a plurality of mating shapes of an implant jig for use in implanting a pedicle screw into the patient's vertebrae during the spinal procedure; and
   transmitting, to a milling device, a milling program based at least on the placement of the mating shapes within the reformatted plurality of two-dimensional images of the patient's vertebrae.

2. The method of claim 1 wherein locating the plurality of mating shapes within the reformatted plurality of two-dimensional images comprises indicating, within at least one of the plurality of two-dimensional images, a position of a rectangular mating shape of the implant jig such that the rectangular mating shape contacts at least one first side and a superior side of a spinous process of the patient's vertebrae as illustrated in the at least one of the plurality of two-dimensional images.

3. The method of claim 1 wherein locating the plurality of mating shapes within the reformatted plurality of two-dimensional images comprises indicating, within the at least one of the plurality of two-dimensional images, a position of a second circular mating shape such that the second circular mating shape contacts a first side lamina, within an inferior vertebral notch, on the first side of the patient's vertebrae as illustrated in the at least one of the plurality of two-dimensional images, the second circular mating shape corresponding to a second tubular mating shape of the implant jig.

4. The method of claim 3 wherein locating the plurality of mating shapes within the reformatted plurality of two-dimensional images comprises indicating, within the at least one of the plurality of two-dimensional images, a position of a third circular mating shape such that the third circular mating shape contacts the vertebrae near a superior facet of a middle portion of the lamina of the patient's vertebrae as illustrated in the at least one of the plurality of two-dimensional images, the third circular mating shape corresponding to a third tubular mating shape of the implant jig.

5. The method of claim 4 wherein locating the plurality of mating shapes within the reformatted plurality of two-dimensional images comprises indicating, within the at least one of the plurality of two-dimensional images, a position of a fourth circular mating shape such that the fourth circular mating shape contacts the vertebrae near an inferior facet of the middle portion of the lamina of the patient's vertebrae as illustrated in the at least one of the plurality of two-dimensional images, the fourth circular mating shape corresponding to a fourth tubular mating shape of the implant jig.

6. The method of claim 5 wherein the locating of the rectangular mating shape of the implant jig provides at least three points of contact to the patient's vertebrae and each of the first circular mating shape, the second circular mating shape, the third circular mating shape, and the fourth circular mating shape provides at least one point of contact on the patient's vertebrae.

7. The method of claim 1 wherein the implant jig comprises:
   a first plurality of contact shapes contacting a lateral aspect of a pedicle of the patient's vertebrae;
   a second plurality of contact shapes contacting a superior portion of a transfer process of the patient's vertebrae; and
   at least one contact shape contacting a posterior portion of the pedicle of the patient's vertebrae.

8. The method of claim 1 further comprising:
   generating the plurality of two-dimensional images of a patient's vertebrae utilizing a computed-tomography imaging machine.

9. The method of claim 1 wherein reformatting the two-dimensional images comprises:
   identifying one or more landmarks on the plurality of two-dimensional images of a patient's vertebrae; and
   reorienting the plurality of two-dimensional images of a patient's joint vertebrae at least on the one or more landmarks.

10. A system for creating an implant jig for a surgical spinal procedure, the system comprising:
    a network connection for receiving a plurality of two-dimensional images of a patient's vertebrae the subject of the spinal procedure, the plurality of two-dimensional images generated utilizing a magnetic-resonance imaging machine; and
    a computing device comprising;
       at least one processing device; and
       a non-transitory memory device in communication with the at least one processing device for storing one or more instructions that, when executed by the at least one processing device, cause the computing device to perform the operations of:
       reformatting at least a portion of the two-dimensional images, via an identification of a plurality of portions of the patient's vertebrae within the plurality of two-dimensional images, to approximate an anatomical coordinate of the patient's vertebrae;
       locating a plurality of mating shapes within the reformatted plurality of two-dimensional images of the patient's vertebrae by receiving an indication, within the at least one of the plurality of two-dimensional images, a position of a first circular mating shape such that the first circular mating shape contacts a superior lamina, between a superior facet and a vertebral canal, on a first side of the patient's vertebrae as illustrated in the at least one of the plurality of two-dimensional images, the first circular mating shape corresponding to a first tubular mating shape of the implant jig, the plurality of mating shapes corresponding to a plurality of mating shapes of an implant jig for use implanting a pedicle screw into the patient's vertebrae during the spinal procedure;

generating a milling program based at least on the placement of the mating shapes within the reformatted plurality of two-dimensional images of the patient's vertebrae; and transmitting the generated milling program over the network connection to a milling device for milling the implant jig based at least on the generated milling program.

11. The system of claim 10 wherein reformatting the two-dimensional images comprises:

receiving an identification of one or more landmarks on the plurality of two-dimensional images of a patient's vertebrae; and reorienting the plurality of two-dimensional images of a patient's vertebrae based at least on the one or more landmarks.

12. The system of claim 10 wherein locating the plurality of mating shapes within the reformatted plurality of two-dimensional images comprises receiving an indication, within at least one of the plurality of two-dimensional images, a position of a rectangular mating shape of the implant jig such that the rectangular mating shape contacts at least one first side and a superior side of a spinous process of the patient's vertebrae as illustrated in the at least one of the plurality of two-dimensional images.

13. The system of claim 10 wherein locating the plurality of mating shapes within the reformatted plurality of two-dimensional images further comprises receiving an indication, within the at least one of the plurality of two-dimensional images, a position of a second circular mating shape such that the second circular mating shape contacts a first side lamina, within an inferior vertebral notch, on the first side of the patient's vertebrae as illustrated in the at least one of the plurality of two-dimensional images, the second circular mating shape corresponding to a second tubular mating shape of the implant jig.

14. The system of claim 13 wherein locating the plurality of mating shapes within the reformatted plurality of two-dimensional images further comprises receiving an indication, within the at least one of the plurality of two-dimensional images, a position of a third circular mating shape such that the third circular mating shape contacts the vertebrae near a superior facet of a middle portion of the lamina of the patient's vertebrae as illustrated in the at least one of the plurality of two-dimensional images, the third circular mating shape corresponding to a third tubular mating shape of the implant jig.

15. The system of claim 14 wherein locating the plurality of mating shapes within the reformatted plurality of two-dimensional images further comprises receiving an indication, within the at least one of the plurality of two-dimensional images, a position of a fourth circular mating shape such that the fourth circular mating shape contacts the vertebrae near an inferior facet of the middle portion of the lamina of the patient's vertebrae as illustrated in the at least one of the plurality of two-dimensional images, the fourth circular mating shape corresponding to a fourth tubular mating shape of the implant jig.

16. The system of claim 10 wherein the implant jig comprises:

a first plurality of contact shapes contacting a lateral aspect of a pedicle of the patient's vertebrae;

a second plurality of contact shapes contacting a superior portion of a transfer process of the patient's vertebrae; and at least one contact shape contacting a posterior portion of the pedicle of the patient's vertebrae.

* * * * *